United States Patent [19] [11] 4,028,350
Bundy [45] June 7, 1977

[54] 9α,11αOR 11α,9αEPOXYMETHANO-PROSTAGLANDANS AND PROCESS FOR THEIR PREPARATION
[75] Inventor: Gordon L. Bundy, Portage, Mich.
[73] Assignee: The Upjohn Company, Kalamazoo, Mich.
[22] Filed: June 25, 1976
[21] Appl. No.: 699,672
[52] U.S. Cl. .............. 260/240 R; 260/347.3; 347.4
[51] Int. Cl.² .............. C07D 307/06; C07D 307/28
[58] Field of Search .............. 260/240 R, 340.5 P, 260/346.2 R, 347.3, 347.4

[56] References Cited
UNITED STATES PATENTS
3,931,297  1/1976  Crabbe .................. 260/240 R X OTHER PUBLICATIONS
Jacobs, P. M. et al., "Synthesis of 3,5 Dialkyl-1,2-dioxalanes" in J. Org. Chem. vol. 39, No. 23 (1974), pp. 3427-3429.
Tetrahedron Letters, No. 10, pp. 737-740, 1976, Corey et al.

Primary Examiner—Allen B. Curtis
Attorney, Agent, or Firm—Robert A. Armitage

[57] ABSTRACT

The present specification provides 9α,11α- epoxymethano or 11α,9α-epoxymethano-9,11,15-trideoxy prostaglandin F analogs, i.e., analogs of

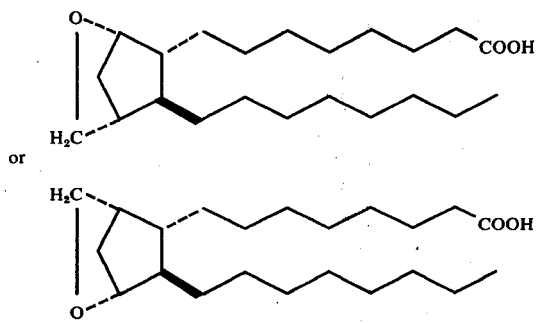

respectively, and a process for their preparation. These compounds are useful anti-inflammatory agents.

58 Claims, No Drawings

9α,11αOR 11α,9αEPOXYMETHANO-PROSTAGLANDANS AND PROCESS FOR THEIR PREPARATION

BACKGROUND OF THE INVENTION

This invention provides novel compositions of matter. This invention further provides novel processes for producing these compositions of matter. This invention further provides novel chemical intermediates useful in the above processes.

This invention is specifically concerned with novel cyclic ethers which are analogs of the compound of the formula:

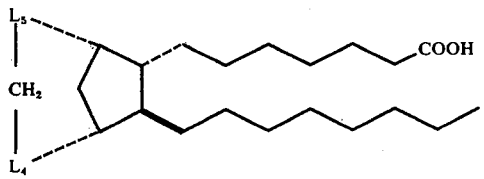

wherein $L_4$ and $L_5$ are —O— or a valence bond with the proviso that one of $L_4$ and $L_5$ is —O— the other is a valence bond. Included within the scope of the invention are compounds of the formulas:

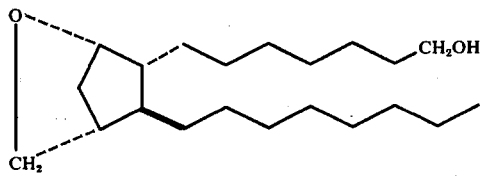

and

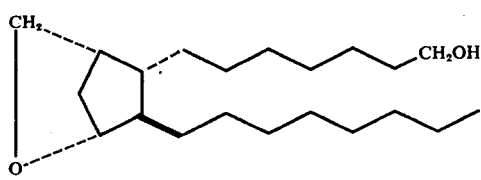

Accordingly, the present invention is concerned with bicyclic ether analogs of the prostaglandins, e.g. 9α,1-1α-epoxymethano- or 11α,9αepoxymethano-prostane:-derviatives. Thus each of the above depicted compounds is a derivative of prostane which has the following structure and carbon atom numbering

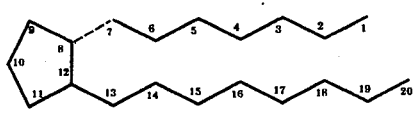

For a discussion of the use of the corresponding C-1 carboxylic acid derivatives, i.e., the prostaglandins, see, for example, Bergstrom et al., Pharmacol. Rev. 20, 1 (1968), and references cited therein. A systematic name for prostanoic acid, the above-mentioned C-1 carboxylic acid, is 7-[(2β-octyl)-cyclopent-1α-yl]-heptanoic acid.

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (∼) herein will represent attachment of substituents in either the alpha or beta configuration or attachment in a mixture of alpha and beta configurations.

Molecules of the known prostaglandins each have several centers of asymmetry, and can exist in racemic (optically inactive form and in either of the two enantiomeric (optically active) forms, i.e. the dextrorotatory and levrotatory forms. As drawn, the above formulas each represent the particular optically active form of the prostaglandin as is obtained from mammalian tissues, for example, sheep vesicular glands, swine lung, or human seminal plasma, from carbonyl and/or double bond reduction of the prostaglandin so obtained. See, for example, Bergstrom et al., ctied above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or "PG" will mean the optically active form of that prostaglandin thereby referred to with the same absolute configuration as $PGE_1$ obtained from mammalian tissues. When reference to the racemic form of one of those prostaglandins is intended, the word "racemic" or "dl" will precede the prostaglandin name.

The term "prostaglandin-type" (PG-type) product, as used herein, refers to any bicyclic cyclopentane derivative which is useful as an antiinflammatory agent, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparation a prostaglandin-type product, each represent the particular stereoisomer of the prostaglandin-type product which is of the same relative stereochemical configuration as a corresponding prostaglandin obtained from mammalian tissues, or the particular stereoiosmer of the intermediate which is useful in preparing the above stereoisomer of the prostaglandin-type product.

The term "prostaglandin analog," as used herein, represents that stereoisomer of a prostaglandin-type product which is of the same relative stereochemical configuration as a corresponding prostaglandin in obtained from mammalian tissues or a mixture comprising that stereoisomer and the enantiomer thereof. In particular, where a formula is used to depict a prostaglandin-type compound herein, the term prostaglandin analog refers to the compound of that formula, or a mixture comprising that compound and the enantiomer thereof.

SUMMARY OF THE INVENTION

The present invention particularly and especially provides
a prostaglandin analog of the formula

[Structure 1]

or

[Structure 2]

wherein $Y_1$ is trans—CH—CH—, —$CH_2CH_2$—, or —C ≡ C—; wherein $L_1$ is

[Structure: R_3, R_4]

[Structure: R_3, R_4]

or a mixture of

[Structure: R_3, R_4]

and

[Structure: R_3, R_4]

wherein $R_3$ and $R_4$ are hydrogen, methyl, or fluoro, being the same or different, with the proviso that one of $R_3$ and $R_4$ is fluoro only when the other is hydrogen or fluoro; wherein $Z_1$ is
1. cis—CH=CH—$CH_2$—$(CH_2)_g$—$CH_2$—,
2. cis—CH=CH—$CH_2$—$(CH_2)_g$—$CF_2$,
3. cis—$CH_2$—CH=CH—$(CH_2)_g$—$CH_2$,
4. —$(CH_2)_3$—$(CH_2)_g$—$CH_2$—,
5. —$(CH_2)_3$—$(CH_2)_g$—$CF_2$—,
6. —$CH_2$—O—$CH_2$—$(CH_2)_g$—$CH_2$—,
7. —C ≡ C—$CH_2$—$(CH_2)_g$—$CH_2$—,
8. —$CH_2$—C ≡ C—$(CH_2)_g$—$CH_2$—,

[Structure: phenyl—$CH_2$—$(CH_2)_g$—], or        (9)

[Structure: phenyl—O—$(CH_2)_g$—],               (10)

wherein $g$ is one, 2, or 3;
wherein $R_7$ is
1. —$(CH_2)_m$—$CH_3$,

[Structure: —O—phenyl—$(T)_s$], or              (2)

[Structure: —(CH)_l—phenyl—$(T)_s$],            (3)

wherein 1 is zero to 3, inclusive,
wherein $m$ is one to 5, inclusive, T is chloro, fluoro, trifluromethyl, alkyl of one to 3 carbon atoms, inclusive, or alkoxy of one to 3 carbon atoms, inclusive, and $s$ is zero, one, 2, or 3, the various T's being the same or different, with the proviso that not more than two T's are other than alkyl, with the further proviso that $R_7$ is

[Structure: —O—phenyl—$(T)_s$]

wherein T and $s$ are as defined above, only when $R_3$ and $R_4$ are hydrogen or methyl, being the same or different; and wherein $X_1$ is
  1. —$COOR_1$:
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
  2. —$CH_2OH$, or
  3. —$CH_2NL_2L_3$,
wherein $L_2$ and $L_3$ are hydrogen, alkyl of one to 4 carbon atoms, inclusive;
with the proviso that $Z_1$ is —$(CH_2)_3$—$(CH_2)_g$—$CH_2$, $Y_1$ is —$CH_2CH_2$—, $R_3$ and $R_4$ are both hydrogen and $R_7$ is —$(CH_2)_m$—$CH_3$, only when $X_1$ is not —$COOR_1$.

Within the scope of the novel prostaglandin analogs of this invention there are represented above:
  a. 9,11,15-trideoxy-9α,11α-epoxymethano-PGF-type compounds when the bicyclic cyclopentane-containing ring is

[Structure]

and
  b. 9,11,15-trideoxy-11α,9α-epoxymethano-PGF-type compounds when the bicyclic cyclopentane-containing ring is

[Structure]

Those prostaglandin analogs herein wherein $Z_1$ is cis—CH=CH—$CH_2$—$(CH_2)_g$—$CH_2$— or cis—CH=λCH—$CH_2(CH_2)_g$—$CF_2$— are named as "$PG_2$" compounds. The latter compounds are further characterized as "2,2-difluoro" PG-type compounds. When $g$ is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$ These additional carbon atoms are considered a though they were inserted between the C-2 and C-3 positions. Accordingly, these additional carbon atoms are referred to as C-2a and C-2b, counting from the C-2 to the C-3 position.

Further when Z$_1$ is —(CH$_2$)$_3$—(CH$_2$)$_g$—CH$_2$— or —(CH$_2$)$_3$—(CH$_2$)$_g$—CF$_2$, wherein g is as defined above, the compounds so described are "PG$_1$" compounds. When g is 2 or 3, the 2a-homo and 2a, 2b-dihomo compounds are described as is discussed in the preceding paragraph.

When Z$_1$ is —CH$_2$—O—CH$_2$—(CH$_2$)$_g$—CH$_2$— the compounds so described are named as "5-oxa-PG$_1$" compounds. When g is 2 or 3, the compounds so described are 2a-homo or 2a,2b-dihomo compounds, respectively, as discussed above.

When Z$_1$ is —C ≡ C—CH$_2$—(CH$_2$)$_g$—CH$_2$—, wherein g is as defined above, the compounds so described are named as "5,6-didehydro-PG$_2$" compounds. When g is 2 or 3, the compounds so described are additionally characterized as 2a-homo or 2a,2b-dihomo compounds, respectively, as is discussed above.

When Z$_1$ is —CH$_2$—C ≡ C—(CH$_2$)$_g$-CH$_2$—, wherein g is as defined above, the compounds so described are named as "4,4,5,5-tetradehydro-PG$_1$" compounds. When g is 2 or 3, the compounds so described are further characterized as 2a-homo or 2a,2b-dihomo compounds, respectively, as is discussed above.

When Z$_1$ is cis—CH$_2$—CH=CH—(CH$_2$)$_g$—CH$_2$—, wherein g is as defined above, the compounds so described are named "cis-4,5-didehydro-PG$_1$" compounds. When g is 2 or 3, the compounds so described are further characterized as 2a-homo or 2a,2b-dihomo compounds, respectively, as discussed above.

For the novel compounds of this invention wherein Z$_1$ is

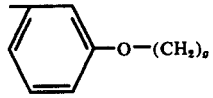

or

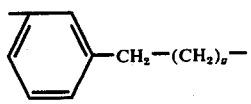

there are described, respectively, 3-oxa-3,7-inter-m-phenylene-4,5,6-trinor- or 3,7-inter-m-phenylene-4,5,6-trinor-PG-type compounds, when g is one. When g is 2 or 3, the above compounds are additionally described as 2a-homo or 2a,2b-dihomo PG-type compounds, respectively.

The novel prostaglandin analogs of this invention which contain a —CH$_2$CH$_2$— or —C ≡ C— moiety at the C-13 to C-14 position, are accordingly, referred to as "13,14-dihydro" or "13,14-didehydro" compounds, respectively.

When R$_7$ is —(CH$_2$)$_m$—CH$_3$, wherein m is as defined above, the compounds so described are named as "19,20-dinor," "20-nor", "20methyl", or "20-ethyl" compounds when m is one, 2, 4, or 5, respectively.

When R$_7$ is

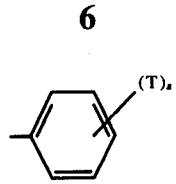

wherein T and s are defined above, the compounds so described are named as "16-phenyl-17,18,19,20-tetranor" compounds, when s is 0. When s is one, 2, or 3, the corresponding compounds are named as "16-(substituted phenyl)-17,18,19,20-tetranor" compounds.

When R$_7$ is

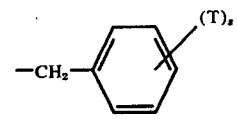

wherein T and s are as defined above, the compounds so described are named as "17-phenyl-18,19,20-trinor" compounds, when s is 0. When is is one, 2, or 3, the corresponding compounds are named as "17-(substituted phenyl)-18,19,20-trinor" compounds.

R$_7$ is

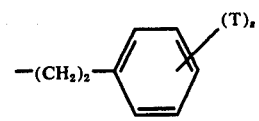

wherein T and s are as defined above, the compounds so described are named as "18-phenyl-19,20-dinor" compounds, when s is 0. When s is one, 2, or 3, the corresponding compounds are named as "18-(substituted phenyl)-19,20-dinor" compounds.

When R$_7$ is

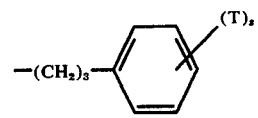

wherein T and s are a defined above, the compounds so described are named as "19-phenyl-20-nor" compounds, when s is 0. When s is one, 2, or 3, the corresponding compounds are named as "19-(substituted phenyl)-20-nor" compounds.

When R$_7$ is

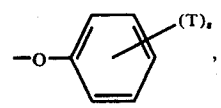

wherein T and s are as defined above, and neither R$_3$ nor R$_4$ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only one of R$_3$ and R$_4$ is methyl or both R$_3$ and R$_4$ are methyl, then the corresponding compounds wherein R$_7$ is as defined in this paragraph are named as "16-phenoxy or 16-(substituted phenoxy)-

18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy compounds discussed above) there are described the "16-methyl" (one and only one of $R_3$ and $R_4$ is methyl)," ,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is —$CH_2OH$, the compounds so described are named as "2-decarboxy-2-hydroxymethyl" compounds.

When $X_1$ is —$CH_2NL_2L_3$, the compounds so described are named as "2-decarboxy-2-aminomethyl or 2-(substituted amino)methyl" compounds.

Accordingly, as indicated by the preceding paragraphs, the novel PG analogs disclosed herein are named according to the system described in Nelson, N. A., J. Med. Chem. 17, 911 (1974).

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of

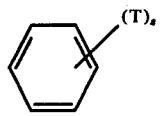

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-) tolyl, (o- m-, or p-)-ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)tirmethylphenyl, (o-, m-, or p-)fluorophenyl, 2-fluoro-(o-, m-, or p-)tolyl, 4-fluro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3- 2,4-, 2,5-, 2,6-, 3,4-, or 3,5-)dichlorophenyl, 4-chloro-3-fluorophenyl, (3- or 4-)chloro-2-fluorophenyl, o-, m-, or p-trifluoromethylphenyl, (o-, m-, or p-)methoxyphenyl, (o-, m-, or p-)ethoxyphenyl, (4- or 5-)chloro-2-methoxyphenyl, and 2,4-dichloro-(5- or 6-)methylphenyl.

The novel prostaglandin analogs of this invention are highly active as inhibitors of the prostaglandin synthetase enzyme system. Regarding prostaglandin synthetase inhibition, see, for example, Vane, Nature New Biology, 231, 232 (1971), Takeguchi et al., Prostaglandins, 2, 169 (1972), and references cited in those. Accordingly, these novel compounds are useful for administration to mammals, including humans, whenever it is desirable medically to inhibit this enzyme system. For example, these novel compounds are useful as anti-inflammatory agents in mammals and especially humans, and for this purpose, are administered systemically and preferably orally. For oral administration, a dose range of 0.05 to 50 mg. per kg. of human body weight is used to give relief from pain associated with inflammatory disorders such as rheumatoid arthritis. They are also administered intravenously in aggravated cases of inflammation, preferably in a dose range 0.01 to 100 µg. per kg. per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

When $X_1$ is —$COOR_1$, the novel PG analogs so described are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araaliphatic amines containing up to and including about 18 carbon atoms, as well as heterocyclic amines, e.g., piperidine, morpholine, pyrroline, piperazine, and lower-alkyl derivatives thereo, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

To obtain the optimum combination of biological response specificity, potency, and duration of activity, certain compounds within the scope of this invention are preferred.

It is preferred that in the carboxy-terminated side chain g be either one or 3, expecially one, i.e., the natural chain length of the prostaglandins. Further when the other chain contains $-(CH_2)_m-CH_3$, it is preferred that me be 3. Further, it is prefered that 1 be zero or one, most preferably one. For those compounds wherein $R_7$ is

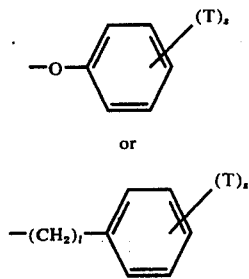

it is preferred that s be zero or one and T be chloro, fluoro, or trifluoromethyl.

For those compounds wherein $R_7$ is

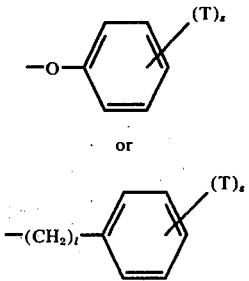

it is preferred that $R_3$ and $R_4$ both be hydrogen.

Especially preferred are those compounds which satisfy two or more of the above preferences. Further, the above preferences are expressly intended to describe the preferred compounds within the scope of any generic formula of novel prostaglandin analogs disclosed herein.

In another aspect of the interpretation of the preferences, herein, each of the bicyclic cylopentane-containing ring structures as employed herein are each representative of a particular "parent structure" which is useful in naming and catagorizing the novel prostaglandin analogs disclosed herein. Further, where a formula depicts one genus of PG analogs disclosed herein evidencing one of these ring structures, then the corresponding genus of PG analogs evidencing the remaining ring structure cited herein for novel prostaglandin analogs is intended to represent an equally preferred genus of compounds. Thus, for example, for each 9,11,15-trideoxy-9α,11α-epoxymethano-PGF-type product depicted by a formula herein, the corresponding genus of 9,11,15-trideoxy-11α,9α-epoxymethano-PGF-type products are equally preferred embodiments.

The Charts herein describe methods whereby the novel prostaglandin analogs of this invention are prepared.

With respect to the Charts $L_1$, $L_2$, $L_3$, $R_1$, $R_7$, $Z_1$, $g$, $m$ and $Y_1$ are as defined above;

$M_{14}$ is

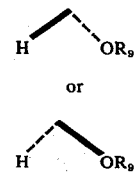

wherein $R_9$ is an acyl protecting group;

Chart A

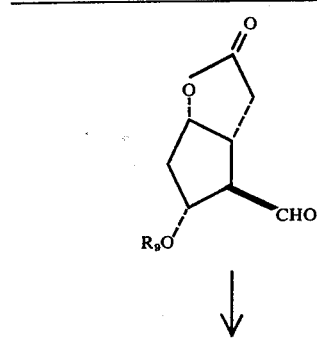

XXI

Chart A-continued
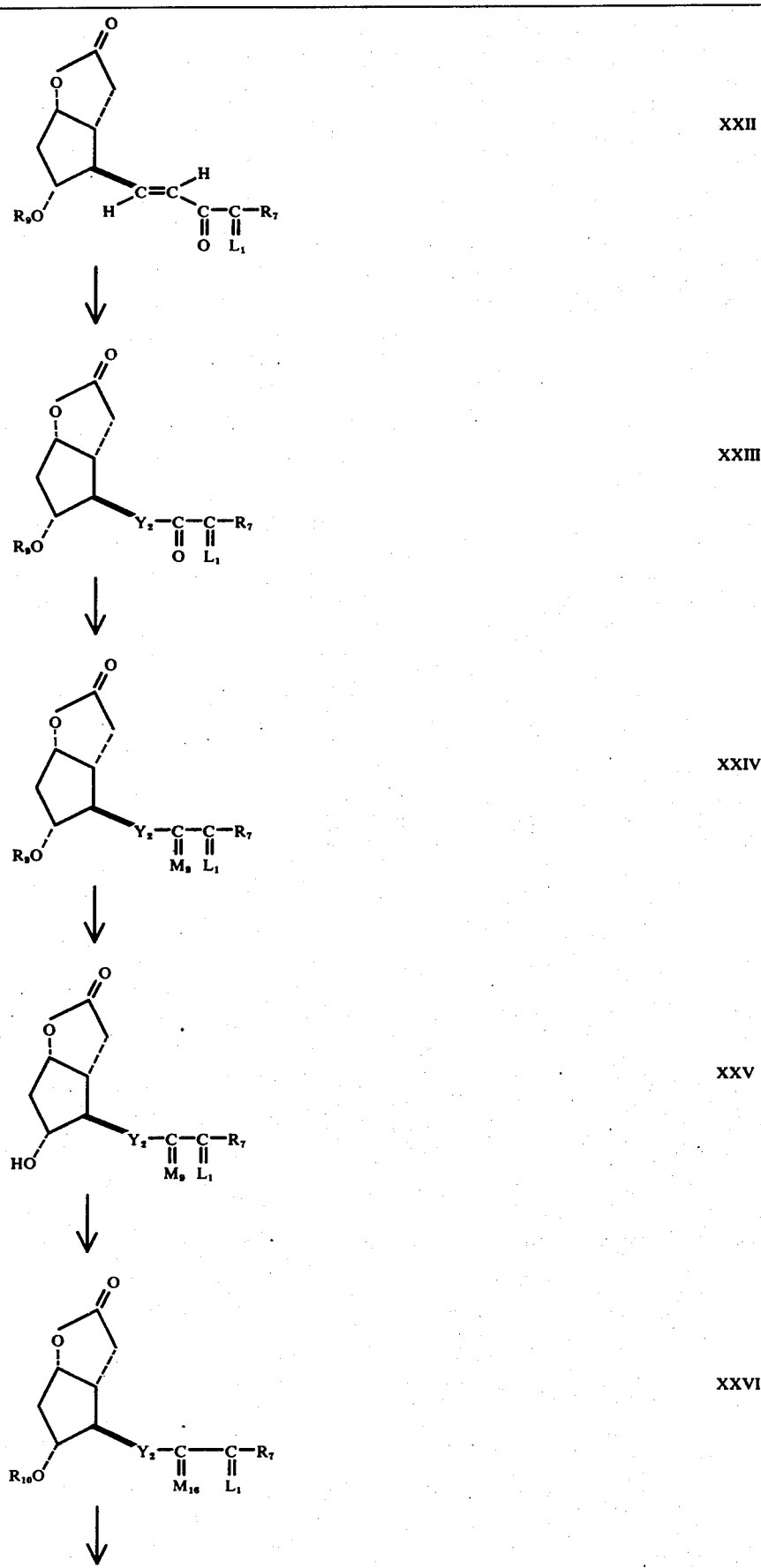
XXII
XXIII
XXIV
XXV
XXVI

Chart A-continued
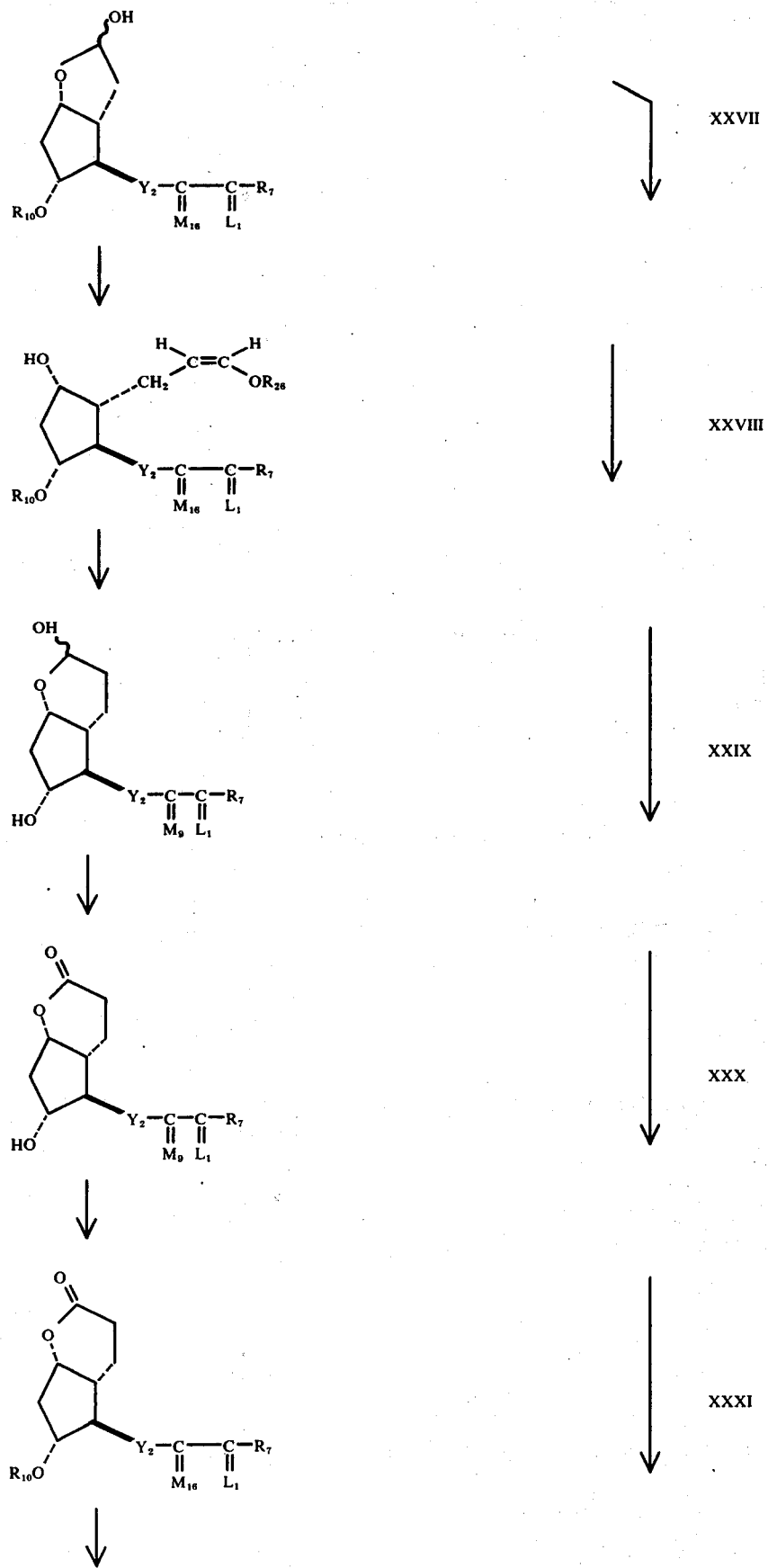

Chart A-continued
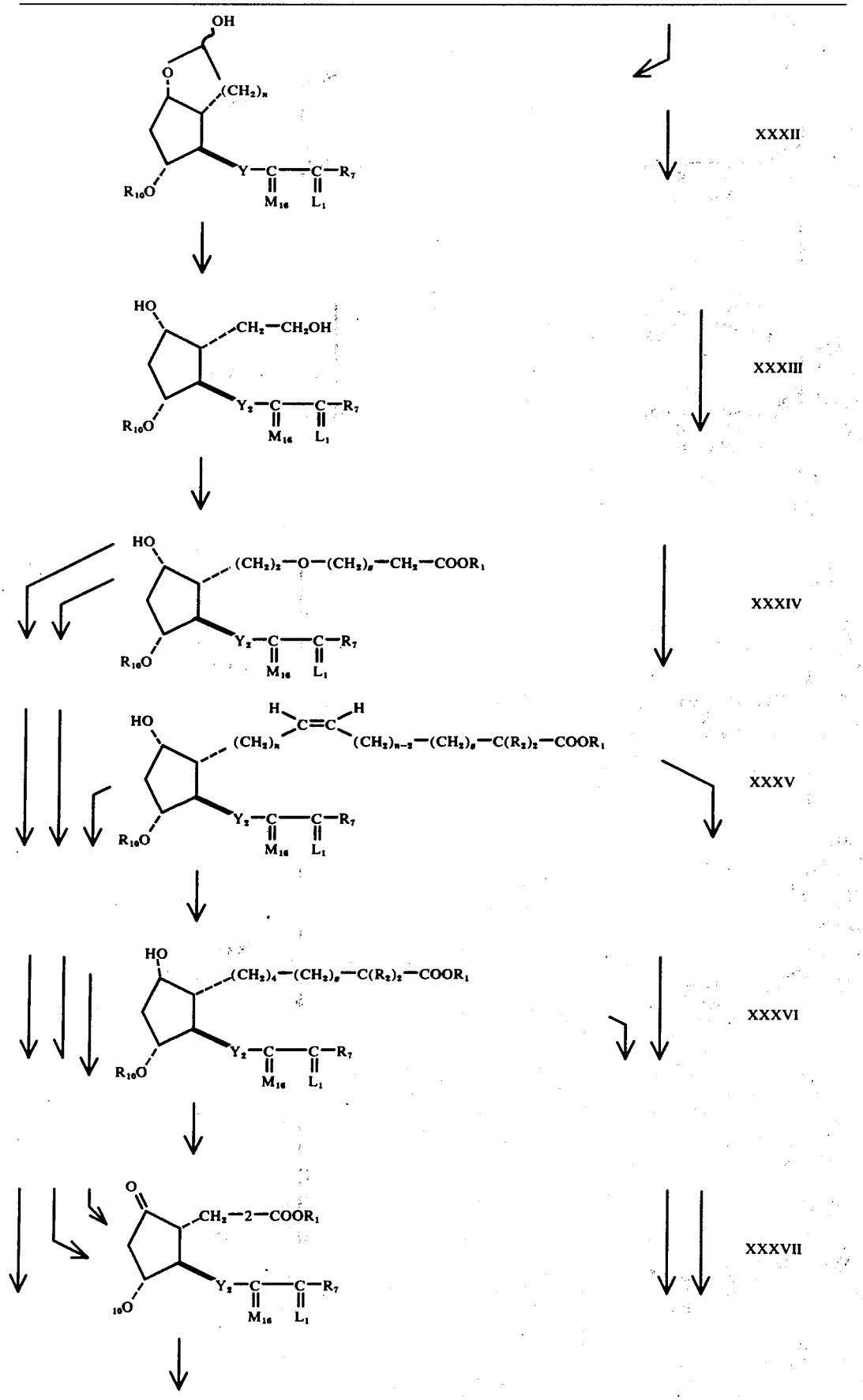
XXXII
XXXIII
XXXIV
XXXV
XXXVI
XXXVII

Chart A-continued
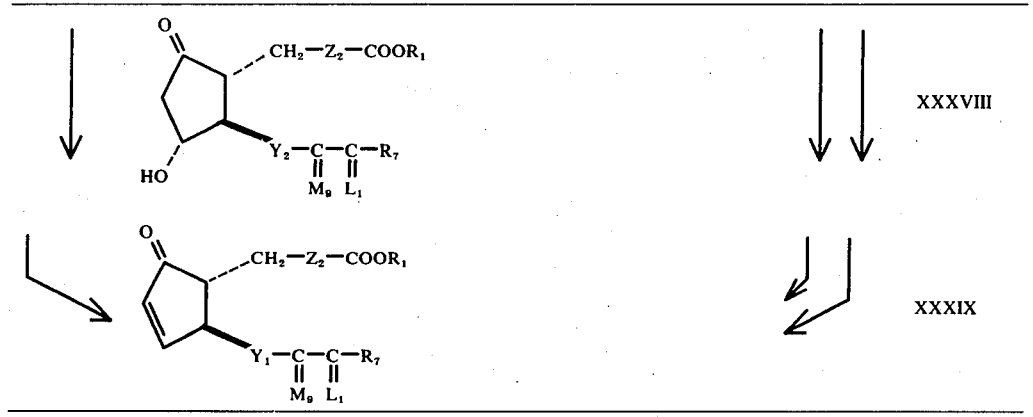
XXXVIII
XXXIX
Chart B
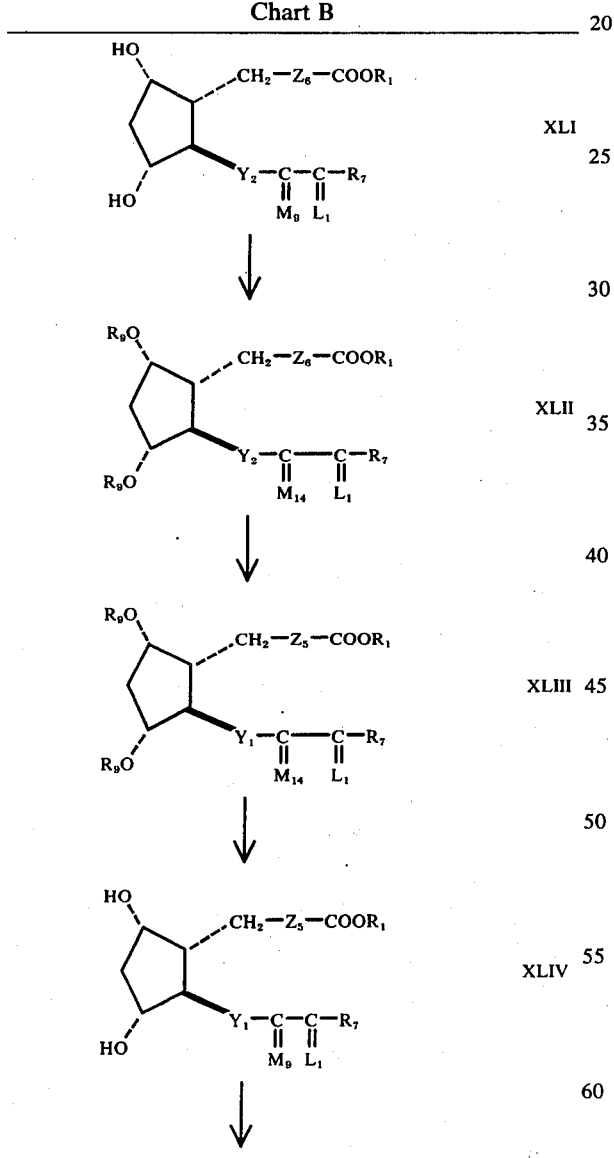
XLI
XLII
XLIII
XLIV
Chart B-continued
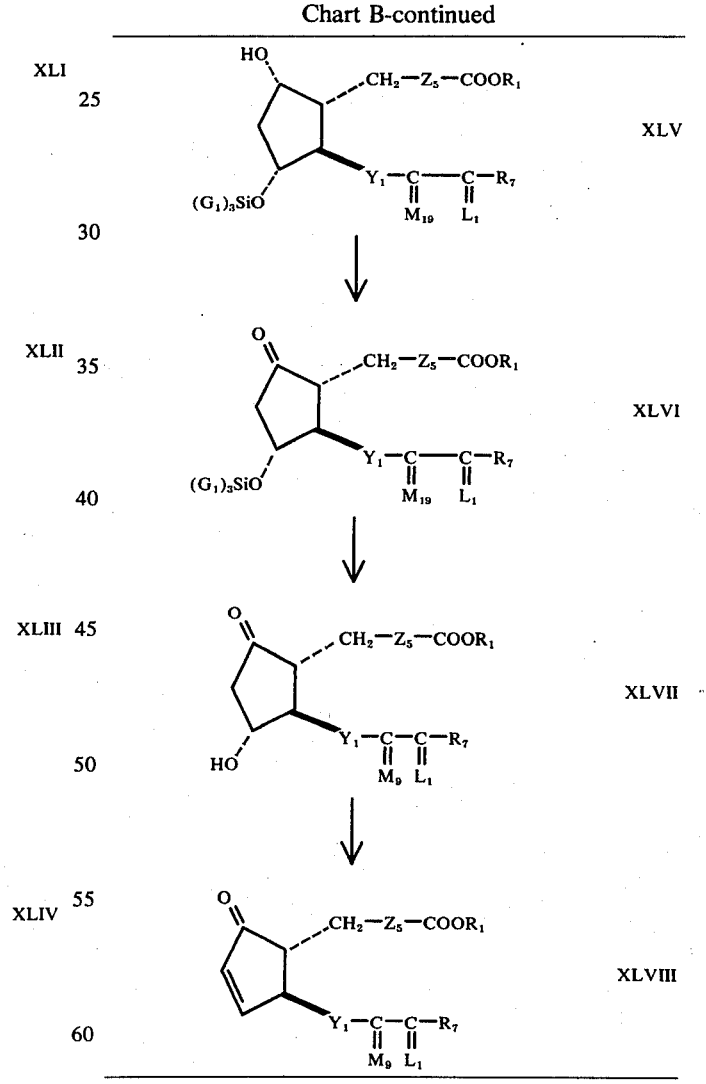
XLV
XLVI
XLVII
XLVIII

Chart C
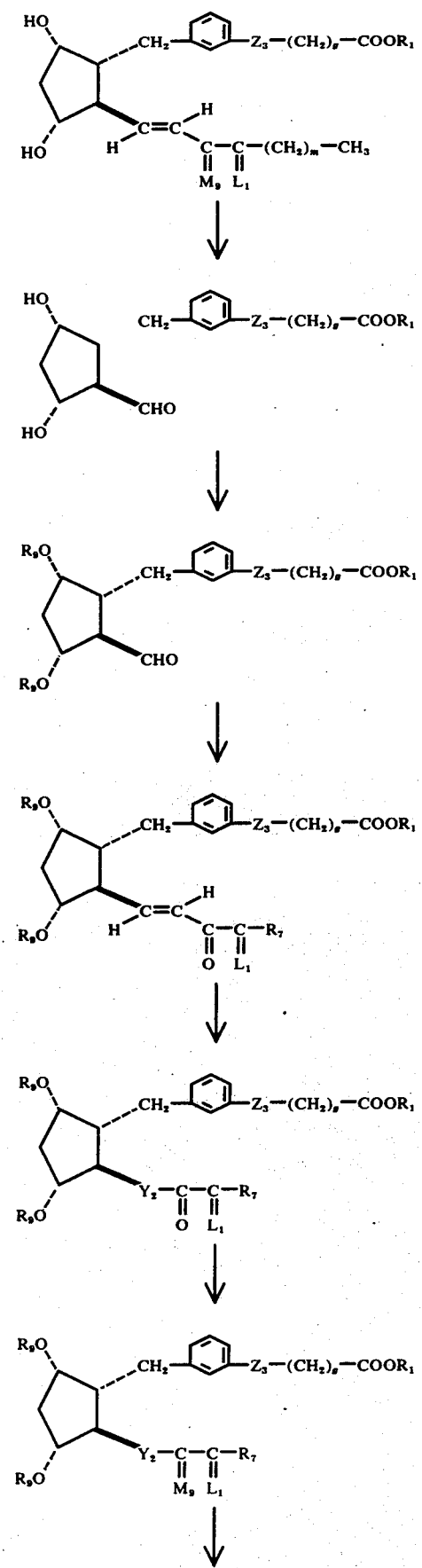
Chart C-continued
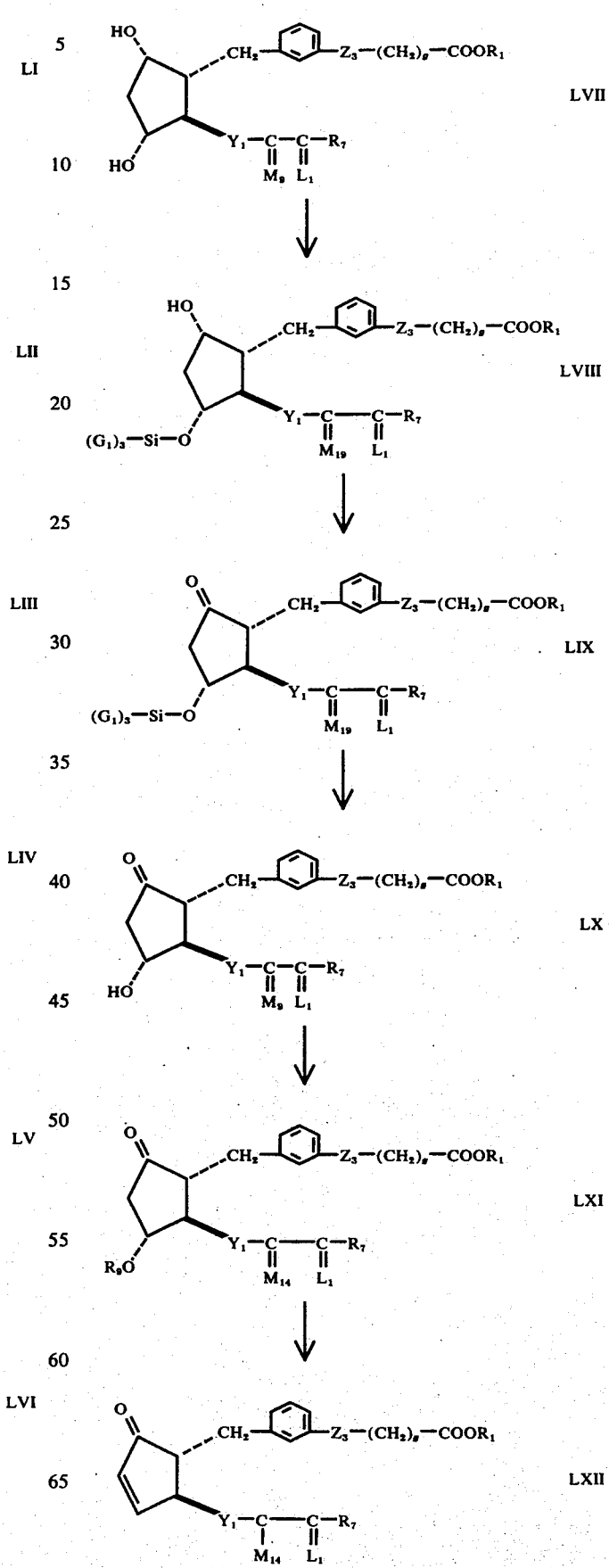

Chart C-continued
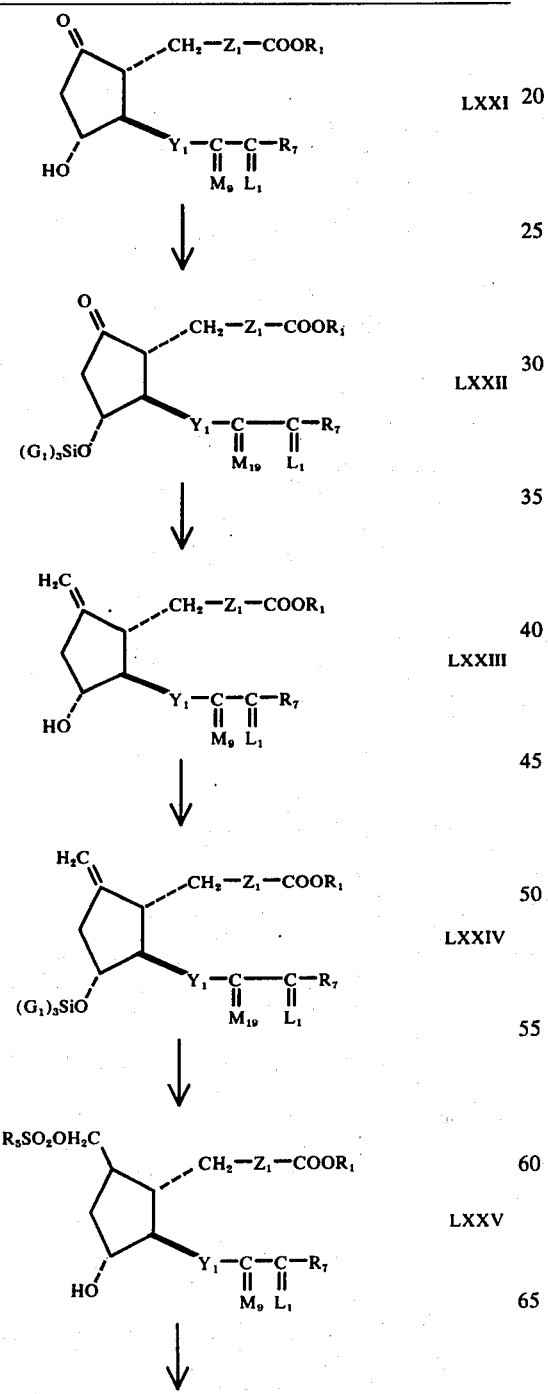
Chart D
Chart D-continued
Chart E
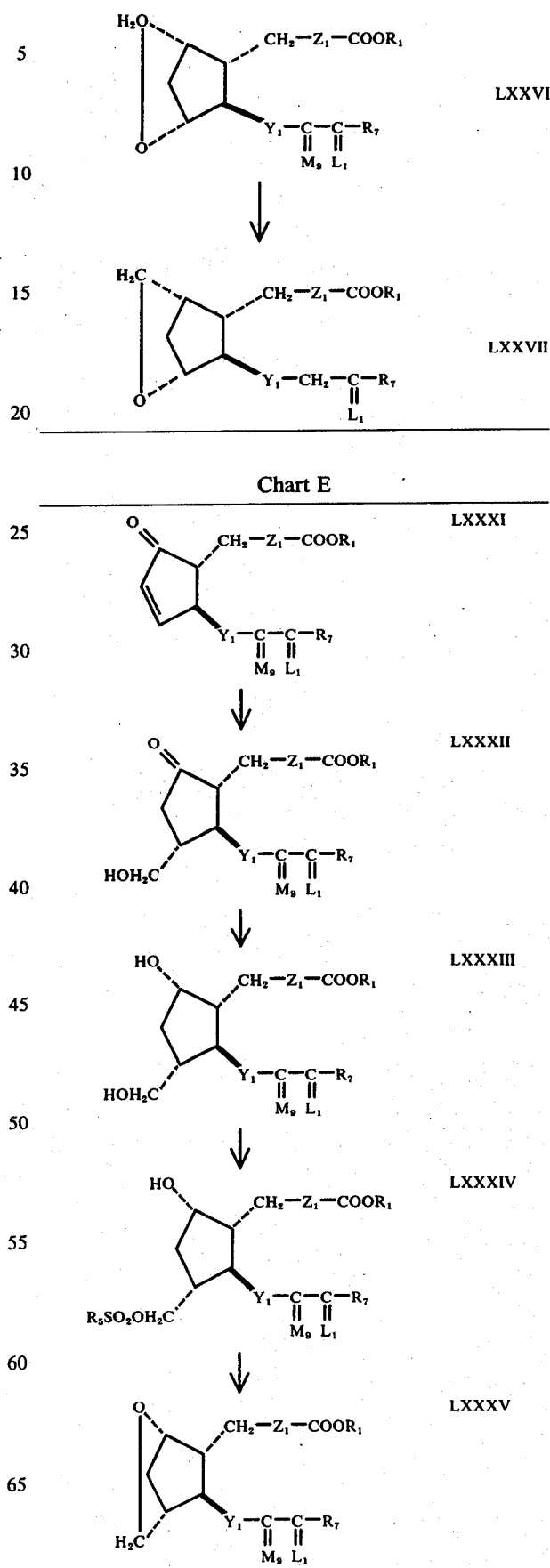

Chart E-continued
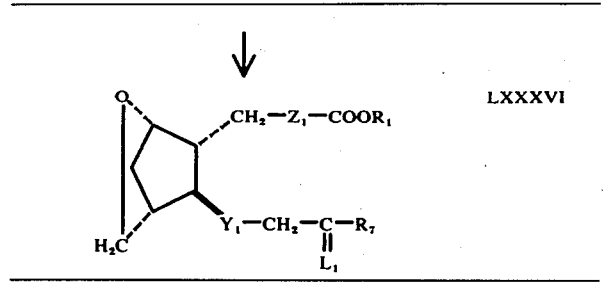
Chart F
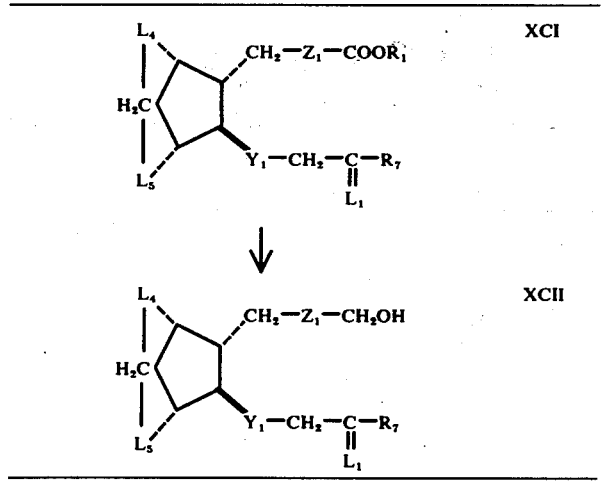
Chart G
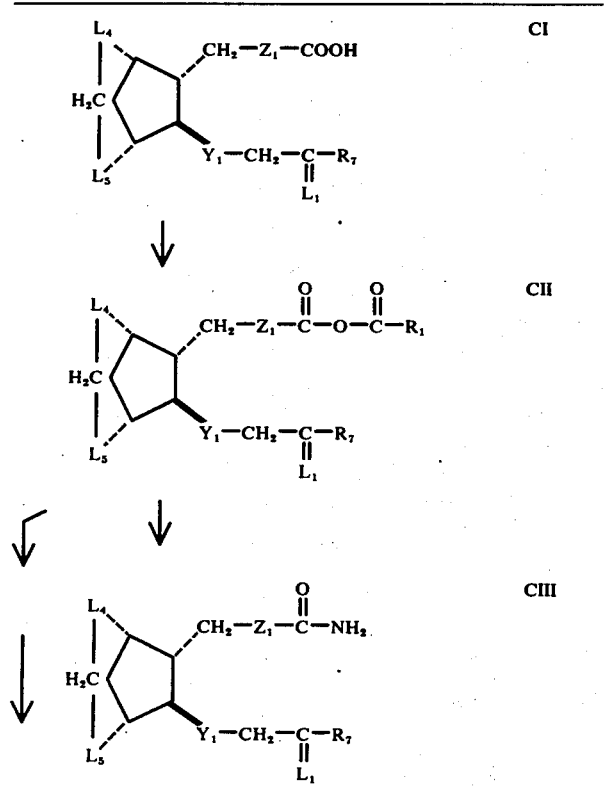
Chart G-continued
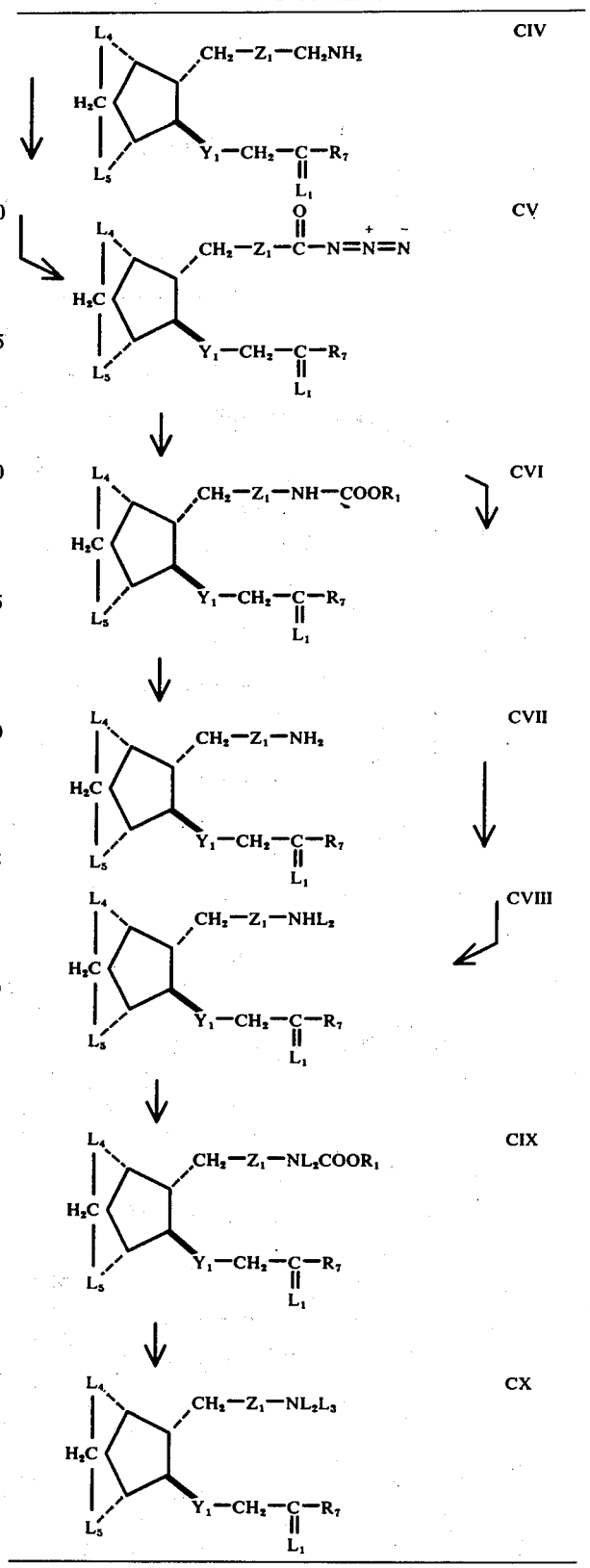
$M_9$ is -continued

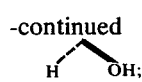

$M_{16}$ is

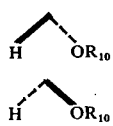

wherein $R_{10}$ is a blocking group;
$M_{19}$ is

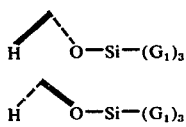

wherein $G_1$ is as defined below;

$R_2$ is hydrogen or fluoro. $R_5$ is a non-reactive, organic radical, as hereinafter further specified, being, for example, alkyl, aralkyl, or aryl. Conveniently $R_5$ is p-tolyl-, so that $R_5SO_2O-$ represents a readily synthesized p-toluenesulfonyl moiety.

$R_{26}$ is hydrocarbyl, including alkyl, aralkyl, cycloalkyl, and the like, Examples of these hydrocarbyl groups include 2-methylbutyl, isopentyl, heptyl, octyl, nonyl, tridecyl, octadecyl, benzyl, phenethyl, p-methylphenethyl, 1-methyl-3-phenylpropyl, cyclohexyl, phenyl, and p-methylphenyl, $G_1$ is alkyl of one to 4 carbon atoms, cycloalkyl of 3 to 10 carbon atoms, inclusive, aralkyl of 7 to 12 carbon atoms, phenyl, or phenyl substituted with one or 2 fluoro, chloro, or alkyl of one to 4 caarbon atoms, with the proviso that in the -Si($G_1$)$_3$ moiety the various $G_1$'s are the same or different.

$R_9$ is an acyl protecting group. Acyl protecting groups according to $R_9$, include:

a. Benzoyl;
b. Benzoyl substituted with one to 5, inclusive, alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;
c. Benzoyl substituted with alkoxycarbonyl of 2 to 5 carbon atoms, inclusive;
d. Naphthoyl;
e. Naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or
f. Alkanoyl of 2 to 12 carbon atoms, inclusive.

In preparing these acyl derivatives of a hydroxycontaining compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or phosphoryl chloride or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9$Hal, wherein Hal is chloro, bromo, or iodo. For example, benzoyl chloride is reacted with the hydroxy-containing compound in the presence of a hydrogen chloride scavenger, e.g., an amine such as pyridine, triethylamine or the like. The reaction is carried out under a variety of conditions, using procedures generally known in the art. Generally mild conditions are employed: 20°-60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides (($R_9)_2O$), or acyl chlorides ($R_9Cl$): benzoyl; substituted benzoyl, e.g., 2-, 3-, or 4-)-methylbenzoyl, (2-, 3-, or 4-)-ethyl benzoyl, (2-, 3-, or 4-)-isopropylbenzoyl, (2-, 3-, or 4-)-tert-butylbenozyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl; 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g., tert-butyl on both of the ring carbon atoms adjacent to the carbonyl attaching cite.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor as reactive to the reagents used in the transformations used herein as an hydroxy is and which is subsequently replaceable with hydrogen in the preparation of the prostaglandin-type compounds. Several blocking groups are known in the art, e.g. tetrahydropyranyl. See for reference E. J. Corey, Proceedings of the Robert A. Welch Foundation Conferences on Chemical Research, 12, Organic Synthesis, pgs. 51-79 (1969). Those blocking groups which have been found useful include a. tetrahydropyranyl;
b. tetrahydrofuranyl; and
c. a group of the formula

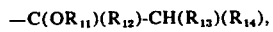

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or $-(CH_2)_b-O-(CH_2)_c-$, wherein $a$ is 3, 4, or 5, or $b$ is one, 2, or 3, and $c$ is one, 2, or 3, with the proviso that $b$ plus $c$ is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 10 times the stoichiometric amount. The reaction is normally complete in less than an hour at 20 to 50° C.

When the blocking group is tetrahydrofuranyl, 2,3-dihydrofuran is used, as described in the preceding paragraph, in place of the 2,3-dihydropyran.

When the blocking group is

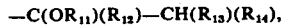

wherein $R_{11}$, $R_{12}$, $R_{13}$, and $R_{14}$ are as defined above, the appropriate reagent is a vinyl ether, e.g., isobutyl vinyl ether or any vinyl ether of the formula

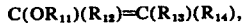

wherein $R_{11}$, $R_{12}$, $R_{13}$, and $R_{14}$ are as defined above; or an unsaturated cyclic or heterocyclic compound, e.g., 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

The symbol $n$ is one or 2.

$Y_2$ is trans—$CH=C(Hal)$—, wherein Hal is chloro, bromo, or iodo, —$CH_2CH_2$—, or trans—$CH=CH$, $Z_2$ is cis—$CH=CH-CH_2-(CH_2)_g-C(R_2)_2-$, cis—$CH_2-CH=CH-(CH_2)_g-CH_2$, —$(CH_2)_3-(CH_2)_g-C(R_2)_2-$, or —$CH_2-O-CH_2-(CH_2)_g-CH_2-$, wherein $R_2$ and $g$ are as defined above.

$Z_3$ is oxa or methylene.

$Z_5$ is —$C \equiv C-CH_2-(CH_2)_g-CH_2-$ or —$CH_2-C \equiv C-(CH_2)_g-CH_2-$.

$Z_6$ is cis—$CH=CH-CH_2-(CH_2)_g-CH_2-$ or cis—$CH_2-CH=CH-(CH_2)_g-CH_2-$.

One of $L_4$ and $L_5$ is oxa, and the other is a valence bond, such that $$\begin{array}{c} L_4 \\ | \\ H_2C \\ | \\ L_5 \end{array}$$

represents $$\begin{array}{c} O \\ | \\ H_2C \end{array}$$

or $$\begin{array}{c} H_2C \\ | \\ O \end{array}$$

Charts A-C herein provide methods whereby starting materials useful for preparing the novel prostaglandin analogs of the present invention according to Charts D-G are prepared.

With respect to Chart A a method is provided whereby the formula XXI bicyclic lactone aldehyde, known in the art in either optically active or racemic form, is transformed to the formula XXXVIII PGE- or formula XXXIX PGA-type compounds. The various reaction steps of Chart A are known in the art.

The formula XXII compound is prepared from the formula XXI comound by a Wittig alkylation. Reagents known in the art or prepared by methods known in the art are employed. The transenone lactone is obtained stereospecifically. See for reference D. H. Wadsworth, et al., Journal of Organic Chemistry 30, 680 (1965).

In the preparation of the formula XXII compound, certain phosphonates are employed in the Wittig reaction. These phosphonates are of the general formula

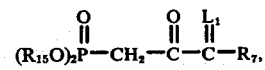

wherein $L_1$ and $R_7$ are as defined above and $R_{15}$ is alkyl of one to 8 carbon atoms, inclusive.

Phosphonates of the above general formula are prepared by methods known in the art. See Wadsworth, et al., as cited above.

Conveniently the appropriate aliphatic acid ester is condensed with the anion of dimethyl methylphosphonate as produced using n-butyllithium. For this purpose, acids of the general formula

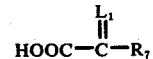

are employed in the form of their lower alkyl esters, preferably methyl or ethyl. The methyl esters for example are readily obtained by reaction of the corresponding acids with diazomethane.

For example, when $R_7$ is

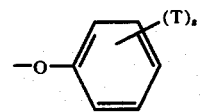

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy,(o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichlorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl- 2-phenoxy- or (2-substituted)phenoxypropionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_7$ is: phenoxy, (o-, m-, or p-)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the $(T)_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is phenyl, benzyl, phenylallyl or substituted phenyl, benzyl, or phenylallyl.

For example, when $R_3$ and $R_4$ of the $L_1$ moiety are both hydrogen and 1 is one there are available the following phenyl or substituted phenyl propionic acids: (o-, m-, or p-)chlorophenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl and 1 is one there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl and 1 is one there are available, for example, the following 2,2-dimethyl-3-phenyl or substituted phenyl propionic acids: phenyl and p-methylphenyl.

When one and only one of $R_3$ and $R_4$ is fluoro and 1 is one there is available, for example, 2-fluoro-3-phenyl propionic acid.

Phenyl substituted acids (as above wherein $R_7$ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted phenylallyl or benzyl chloride. Thus, the above acid is obtained by the following reaction (when 1 is not zero):

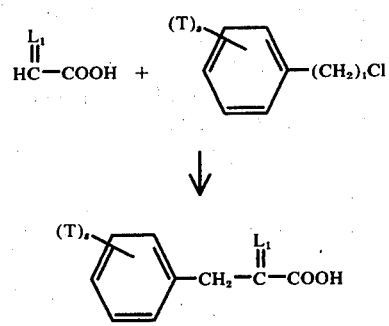

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when one of $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxoalkanoic acids, i.e. butyric, pentanoic, hexanoic, heptanoic, and octanoic. The transformation of these 2-oxo-alkanoic acids to the corresponding 2,2-difluoro alkanoic acids proceeds by methods known in the art, using known ketonic fluorinating reagents. For example, $MoF_6 \cdot BF_3$ is advantageously employed in the fluorination. See Mathey, et al., Tetrahedron Lett. 27, 2965 (1971).

The formula XXIII compound wherein $Y_2$ is trans—CH=C(Hal)— is prepared from the formula XXII compound by dihalogenation, followed by dehydrohalogenation. The halogenation proceeds by methods known in the art, conveniently by reaction of the formula XXII compound with a reagent such as N-halosuccinimide. The reaction proceeds slowly to completion, ordinarily within three to 10 days. Alternatively the molecular form of the halide $(Hal)_2$ in a diluent (e.g., carbon tetrachloride or a mixture of acetic acid and sodium acetate) is employed in this dihalogenation. Thereafter dehydrohalogenation proceeds by addition of an organic base, preferably amine base, to the halide. For example pyridine, or a diazobicycloalkene, is an especially useful amine base, although non-amine bases such as methanolic sodium acetate are likewise employed.

Optionally the formula XXIII compound wherein $Y_1$ is —CH=C(Hal)— is prepared directly from the formula XXI compound using a Wittig reagent derived from a 1-halophosphonate corresponding to the phosphonate described above for the preparation of the formula XXII compound. These phosphonates are known in the art or are readily prepared by methods known in the art. For example, a phosphonate as described above is transformed to the corresponding 1-halophosphonate by dripping the molecular halogen into a solution of the phosphonate and a strong organic base, e.g. sodium methoxide.

The 1-halophosphonate as prepared above is then reacted with the formula XXI compound in a manner described for the preparation of the formula XXII compound from the formula XXI compound to prepare the formula XXIII compound.

In any event, the 14-chloro rather than 14-bromo or 14-iodo intermediates are preferred formula XXIII products, in that they lead to PG intermediates which are more easily dehydrohalogenated at C-13 and C-14 according to the procedures hereinafter described.

In each of the above described methods for the preparation of the formula XXIII compound wherein $Y_2$ is trans-CH=C(Hal)- the desired formula XXIII product is often contaminated with its corresponding cis isomer. In performing the below steps it is particularly desirable to obtain pure formula XXIII product in order to avoid creation of complicated mixtures of stereoisomers. Accordingly, the formula XXIII compound is subjected to conventional separation techniques (e.g. chromatography) to obtain pure product.

The formula XXIII compound wherein $Y_2$ is —CH$_2$C-H$_2$— is prepared from the formula XXII compound by catalytic hydrogenation, employing methods known in the art.

The formula XXIV compound is prepared from the formula XXIII 3-oxo bicyclic lactone by transformation of the 3-oxo-moiety to the $M_9$ moiety.

The above 3-oxo bicyclic lactone is transformed to the corresponding 3α or 3β-hydroxy bicyclic lactone wherein $M_9$ is

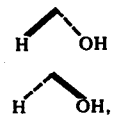

or by reduction of the 3-oxo moiety, followed by separation of the 3α- and 3β-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium(tri-tert-butoxy)-aluminum hydride, metal trialkyl borohydrides, e.g. sodium trimethoxy borohydride, lithium borohydride, and the like. In those cases in which carbon-carbon double bonds are not present, the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

The formula XXV compound is prepared from the formula XXIV compound by deacylation, as described above. The formula XXVI compound is then prepared from the formula XXV compound by replacing any free hydroxy moieties with blocking groups according to $R_{10}$ by the procedure described above. The formula XXVII compound is then prepared from the formula XXVI compound by reduction of the formula XXVI lactone to a lactol. Methods known in the art are employed. For example, diisobutylaluminum hydride is employed at −60° to −70° C.

The formula XXVII compound undergoes condensation to form the formula XXVIII enol ether. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below −10° C. The formula XXVII lactol is mixed with the above reagent and the condensation proceeds smoothly within the temperature range of −30° C. to +30° C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxy- methylenetriphenylphosphorane. Various hydrocarbyloxymethylenetriphenylphosphoranes which are optionally substituted for the alkoxymethylenetriphenylphosphoranes and are accordingly useful for preparing the formula XXVII intermediates wherein $R_{26}$ is hydrocarbyl, include alkoxy-, aralkoxy-, cycloalkoxy-, and aryloxymethylene-triphenylphosphoranes. Examples of these hydrocarbyloxytriphenylphosphoranes are 2-methyl butyloxy-, isopentyloxy-, heptyloxy-, octyloxy-, nonyloxy-, tridecylethyloxy-, 1 -methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346–348, John Wiley and Sons, New York, New York, (1965). The formula XXVIII enol intermediates are then hydrolyzed to the formula XXIX lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXX compound is then prepared from the formula XXIX compound by oxidation of the formula XXIX lactol to a lactone. This transformation is carried out, using for example, silver oxide as an oxidizing reagent, and is followed by treatment with pyridine hydrochloride. Preparation of the formula XXXI compound proceeds from the formula XXX compound by transformation of any free hydroxy moieties to blocking groups according to $R_{10}$, following the procedures herein described for such a transformation.

Thereafter the formula XXXII compound (wherein n is 2) is prepared from the formula XXXI compound by reduction of the formula XXX lactone to a lactol. For example, diisobutylaluminum hydride is employed as is described above for the reduction of lactones to lactols. The formula XXXII lactol is alternately represented by the formula XXVII compound when n is one.

The formula XXXV compound is prepared from the formula XXXII compound by a Wittig alkylation, using the appropriate ($\omega$-carboxyalkyl)triphenylphosphonium bromide with sodio dimethyl sulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXV cis-4,5-didehydro-$PGF_{1\alpha}$ - or $PGF_{2\alpha}$ - type compound.

The formula XXXVI compound is then prepared from the formula XXXV compound by catalytic hydrogenation of the formula XXXV compound. Methods known in the art for transformation of $PG_2$-type compounds to $PG_1$-type compounds are employed. Accordingly, metal catalysts (e.g. palladium) on a suitable support (e.g. carbon) at about 0° C. are employed under a hydrogen atmosphere. See for reference B. Samuelsson, Journal of Biological Chemistry, 239, 491 (1974).

The formula XXXII lactol is transformed into the corresponding formula XXXIV 5-oxa-$PGF_{1\alpha}$ -type intermediate first by reduction of the formula XXXII lactol, for example, with aqeuous methanolic or ethanolic sodium borohydride to the formula XXXIII compound. Alternatively, and preferably, the formula XXXIII compound is obtained by a one step reduction of the formula XXVI lactone, for example, with lithium aluminum hydride or diisobutyl aluminum hydride at a temperature ranging from 0° to 35° C. For preparing the formula XXXIV compound, a Williamson synthesis is employed. For example, the formula XXXII compound is condensed with a haloalkanoate within the scope of

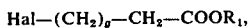

wherein Hal is chloro, bromo, or iodo and g is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at −20° to 50° C., but is preferably performed at ambient temperature. Following the condensation, the formula XXXIV compound is obtained by methods known in the art, for example, by hydrolysis in cold dilute mineral acid.

Thereafter, the formula XXXVII compound is prepared from the formula XXXIV, XXXV, or XXXVI compound by oxidation of the 9-hydroxy to a 9-oxo. Oxidation methods known in the art for the transformation of PGF-type compounds to corresponding PGE-type compounds are employed. For example, the Jones reagent or the Collins reagent is advantageously used.

The formula XXXVIII compound is then prepared from the formula XXXVII compound by first hydrolyzing any blocking groups according to $R_{10}$ and thereafter separating any mixed C-15 epimers. Acidic conditions are employed in the hydrolysis as is described above.

Finally the formula XXXIX compound is prepared from the formula XXXIV, XXXV, or XXXVI compound by first hydrolysing the block groups according to $R_{10}$ (as hereinabove described); dehydrohalogenating with base the resulting product (as described in Chart B) and finally selectively silylating, oxidizing, disilylating, acylating, dehydrating, and deacylating as described in Chart C for the analogous transformation of the formula LVII compound to the formula LXV compound.

Chart B provides a method whereby the formula XLI compound, prepared according to Chart A, is transformed to a formula XLVII 5,6-didehydro-$PGE_2$- or 4,4,5,5-tetradehydro-$PGE_1$-type compound.

The formula XLII compound of Chart B is prepared from the formula XLI compound by replacing free hydroxy hydrogens with acyl protecting groups, according to $R_9$, following the procedure described above. Thereafter the formula XLII compound is transformed to the formula XLII 5,6-didehydro-$PG_2$-type compound or 4,4,5,5-tetradehydro-$PG_1$-type compound by halogenation (bromination or chlorination) followed by dehydrohalogenation.

The halogenation described above consists of transforming the formula XLII $PGF_{2\alpha}$ -type compound to a corresponding 5,6-dihalo-$PG_1$-type compound or transforming the formula XLII cis-4,5-didehydro-$PGF_{1\alpha}$ - type compound to a corresponding 4,5-dihalo-$PGF_{1\alpha}$ -type compound. This halogenation proceeds by mixture of the molecular halogen (e.g. $Br_2$ or $Cl_2$) with the formula XLII compound in a diluent which comprises a chlorinated hydrocarbon. Preferred reaction temperatures are between −40° and 0° C. with −20° C. being especially preferred. Chlorinated hydrocarbon intermediates preferred as diluents include carbon tetrachloride, chloroform, and dichloromethane. Thereafter, the formula XLIII compound is prepared by dehydrohalogenation with base. Amine bases are especially preferred, and in particular 1,5-diazobicyclo[5.4.0.]undecene-5 is preferred. See Fieser and Fieser, Vol. 2, page 101 (1969). Thereafter, the formula XLIV compound is prepared from the formula XLIII compound by deacylation, following procedures described hereinabove.

Alternatively, dehydrohalogenation and deacylation are achieved in one step, employing potassium t-butoxide in dimethylsulfoxide.

When the above reactions hydrolyze an ester, the ester moiety is conveniently restored employing esterification methods described below.

Transformations XLIV to XLVII provide a method whereby the formula XLIV PGF$\alpha$-type compound is transformed into the corresponding PGE-type compound by selective silylation of all secondary hydroxy hydrogens of the formula XLIV compound, other than the C-9 hydroxy.

The formula XLV compound is prepared from the formula XLIV compound by selective silylation of the various secondary hydroxy groups of the formula XLIV compound other than the C-9 hydroxy. Silyl groups with the scope —$Si(G_1)_3$, wherein $G_1$ is alkyl of one to 4 carbon atoms, inclusive, aralkyl of 7 to 12 carbon atoms, inclusive, phenyl, phenyl substituted with one or 2 chloro, fluoro, or alkyl of one to 4 carbon atoms, inclusive, with the proviso that the various $G_1$—s of of the —Si($G_1$)$_3$ moiety are the same or different, are employed. These reagents are known in the art and their use is known in the art.

For the selective silylation procedure methods known in the art for selective silylation of known prostanoic acid derivatives are employed. See for reference U.S. Pat. No. 3,822,303 (issued July 2, 1974), German Offenlegungschrift 2,259,195 (Derwent Farmdoc CPI 36457U-B), and Netherlands Patent 7,214,142 (Derwent Farmdoc CPI 26221U-B).

Examples of the -Si($G_1$)$_3$ moiety are trimethylsilyl, dimethyl(tert-butyl)silyl and dimethylphenylsilyl. Examples of alkyl of one to 4 carbon atoms, inclusive, aralkyl of 7 to 12 carbon atoms, inclusive, and phenyl or substituted phenyl moieties are provided hereinabove.

The formula XLVI compound is prepared from the formula XLV compound by oxidation of the C-9 hydroxy to a C-9 oxo. Oxidation reagents and methods known in the art are employed. For example, the Jones or especially Collins Reagent is advantageously employed.

The formula XLVII compound is prepared from the formula XLVI compound by hydrolysis of the silyl groups. Hydrolysis proceeds by methods known in the art, e.g. the use of water or dilute aqueous acetic acid in a diluent of water and a quantity of a water miscible solvent sufficient to yield a homogeneous reaction mixture. This hydrolysis is ordinarily complete within 2 to 12 hr. at 25° C., and is preferably carried out in an atmosphere of an inert gas such as nitrogen or argon.

Finally the formula XLVII compound is transformed to the corresponding formula XLVIII compound by methods known in the art for the transformation of PGE-type compounds to PGA-type compounds. See for example the transformation of the formula LX compound to the formula LXII compound of Chart C.

Chart C provides a method whereby the formula LI 3,7-inter-m-phenylene- or 3,7-inter-m-phenylene-3-oxa-PGF$\alpha$ -type compound is transformed to corresponding formula LX PGE-type or formula LXV PGA-type compounds. The compounds according to formula LI which are employed as starting material for Chart C are known in the art or readily available by methods known in the art. For example, see U.S. Pat. No. 3,933,900, particularly Chart L therein which describes the preparation of 3,7-inter-m-phenylene-3-oxa-4,5,6-trinor-PGF$_{2\alpha}$ -type compounds.

With respect to Chart C, the formula LII compound is prepared from the formula LI compound by cleavage of the 13,14-trans double bond, conveniently by ozonolysis. Ozonolysis proceeds by bubbling dry oxygen, containing about 3 percent ozone, through a mixture of a formula LI compound in a suitable nonreactive diluent. For example, n-hexane is advantageously employed. The ozone may be generated using methods known in the art. See, for example, Fieser, et al., "Reagents for Organic Synthesis," John Wiley and Sons, Inc. (1967), pages 773-777. Reaction conditions are maintained until the reaction is shown to be complete, for example, by silica gel thin layer chromatography or when the reaction mixture no longer rapidly decolorizes a dilute solution of bromine in acetic acid.

The formula LIII compound is prepared from the formula LII compound by acylation, employing methods described above for introducing acyl protecting groups according to $R_9$. The formula LIV compound is then prepared from the formula LIII compound employing a phosphonate of the formula:

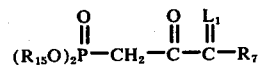

wherein $R_{15}$, $L_1$, $R_7$ are as defined above. Phosphonates of this general formula are prepared by methods known in the art. See the text hereinabove accompanying Chart A for discussion of the preparation and the appropriate reaction conditions by which the Wittig reaction proceeds. The formula LV compound is prepared from the formula LIV compound by transformation of the C-13 to C-14 trans-CH=CH-moiety to an Y$_2$moiety. Methods in Chart A above are employed.

The employed LV compound is then transformed to the corresponding formula LVI compound by transformation of the 15-keto to an $M_9$ moiety, employing methods described above in Chart A.

Thereafter the formula LVI compound prepared above is transformed to the formula LVII compound by deacylation, employing methods described above for removal of acyl protecting groups according to $R_9$, followed by a chromatographic separation of C-15 epimeric mixtures, followed by dihydrohalogenation with base as described in Chart B.

The formula LVII compound is then transformed to the formula LVIII compound and thereafter successively to the formula LIX and formula LX compounds by the methods described in Chart B for the transformation of the formula XLIV compound to the corresponding formula XLVII compound.

The transformation of the formula LX compound to the corresponding formula LXI compound proceeds by acylation. Particularly and especially it is preferred to prepare the formula LXI 11-acetate or 11,15-diacetate. The relatively unstable formula LXI compound is then readily dehydrated yielding the formula LXII PGA-type product. This formula LXII compound is prepared either by allowing the formula LXI compound to spontaneously lose acetic acid, ordinarily within one to 5 days, or if a more rapid dehydration is required mild acidic conditions, such as exposure to silica gel, are employed.

Finally, the formula XLV PGA-type compound is prepared from the formula LXII compound by exzymatic diesterification. Methods described hereinbelow for the removal of C-1 esters are employed.

Chart D provides a method whereby the PGE-type compounds described in the preceeding charts are transformed to corresponding formula LXXVII 9,11,15-trideoxy-11$\alpha$,9$\alpha$-epoxymethano-PGF-type compounds.

The formula LXXI starting material of Chart D is herein employed, or alternatively, the corresponding 14-halo compound as prepared in Chart A, is employed. Thus, when a 14-halo compound is employed in place of the formula LXXI compound the corresponding 14-halo product corresponding to formula LXXVII is prepared. This 14-halo product is then dehydrohalogenated by the procedure described hereinabove for the dehydrohalogenation of 5,6-dihalo compounds of Chart B. The formula LXXII compound of Chart D is prepared from the formula LXXI compound by silylation of the secondary hydroxyls of the formula LXXI compound. Silylation proceeds by methods known in the art, employing the various silyl groups described in preceding Charts. See for example Post "Silicones and Other Organic Silicone Compounds," Reinhold Publishing Co., New York, New York (1949) and Pierce, "Silylation of Organic Compunds,"; Pierce Chemical Co., Rockford, Ill. (1968).

The transformation of the formula LXXII ketone to the corresponding formula LXXIII methylene compound proceeds by methods known in the art. Particularly and especially the procedure disclosed by Johnson, et al., Journal of the American Chemical Society 95, 6462 (1973) is employed.

The procedure first requires the generation of the carbanion of an N-alkyl derivative of an S-methyl-S-arylsulfoximine, for example the carbanion of N,S-dimethyl-S-phenylsulfoximine (i.e., N-methylphenyl-sulfonamidoylmethyl anion as discussed by Johnson above). This carbanion is generated by reacting the corresponding N-alkyl-S-methyl-S-arylsulfoximine with any of the usual reagents which will extract an active hydrogen from such sulfoximines, for example, an alkyl lithium or alkyl magnesium halide. The formula LXXII compound is then mixed with the carbanion thusly generated, and the resulting material mixed with aluminum amalgam in the presence of acetic acid and water to yield the formula LXXIII product (any silyl groups of the formula LXXII compound being removed by the acetic acid).

In the above process the use of a slight excess of the N-alkyl-S-aryl-S-methylsulfoximine molecular equivalent of formula LXXII compound is preferred. One molecular equivalent of the hydrogen extracting reagent, e.g. methyl magnesium chloride or butyl lithium, is used for each equivalent of sulfoximine. The reaction of the carbanion with the formula LXXII compound is carried out in the range of about 0° to −100° C., preferably below about −50° C. An inert reaction diluent is employed, preferably one which is adapted for ease of isolation of reaction products, and is readily miscible with water. Accordingly, tetrahydrofuran is a suitable reaction diluent for the present purposes.

When the reaction of the formula LXXII compound with the carbanion is complete, the resulting product is isolated by procedures known in the art or alternatively the entire reaction mixture is used in the subsequently required reaction with the aluminum amalgam.

This treatment with aluminum amalgam is carried out by contacting the reaction product of the formula LXXII compound with a carbanion with aluminum amalgam, advantageously prepared as in Johnson, et al., cited above, in the presence of aqueous acetic acid and at a temperature range of about 0°–50° C., preferably in the range of about 20°–30° C. Other carboxylic acids are alternatively employed in place of acetic acid, for example, propionic acid, butyric acid, and citric acid. Mineral acids, e.g., hydrochloric acid, are also useful for this purpose. The amounts of aluminum amalgam and acetic acid are not critical, provided that sufficient molecular equivalents of each are used to reduce each molecular equivalent of the carbanion-formula LXXII reaction product. The use of a large excess of aluminum amalgam and acid are however preferred. The amount of water present in the reaction mixture is not critical, provided, however, that sufficient water is present to provide an ionizing reaction system. Also, a sufficient quantity of water miscible inert organic diluents is employed to provide a mobile and substantially homogeneous reaction mixture (except with regard to the aluminum amalgam).

In the event that the preceeding reaction fails to hydrolyze any silyl group at C-11 or C-15, the remaining silyl groups are removed by methods known in the art, e.g., dilute aqueous citric acid, phosphoric acid, and the like. In any event, the formula LXXIII compound results. However, it is not necessary or desirable to assure complete desilylation, since silyl groups are reintroduced in the subsequent reaction step.

The formula LXXIV compound is then prepared from the formula LXXIII compound by silylation, employing, methods, procedures, and reactants described in silylation procedures hereinabove (e.g., the transformation of the formula LXXI compound to the formula LXXII compound).

Thereafter, the formula LXXIV compound is transformed to the formula LXXV compound by a three-step chemical synthesis.

The first step in this synthesis is a combination of hydroboration and oxidation which transforms the 9-methylene group of LXXIV to a 9-hydroxymethyl group ($-CH_2OH$). Hydroboration-oxidation processes are known in the art for hydrating olefinic double bonds. See, for example, Zweifel et al., "Organic Reactions", Volume 13, Chapter 1, John Wiley and Sons, Inc., New York (1963). An especially suitable hydroboration reagent for step (5) of Chart 11 is 9-borabicyclo-[3.3.1]nonane, also known as 9-BBN. See Knights et al., J. Am. Chem. Soc. 90, 5280 (1968); ibid, 5281. Procedures useful for the hydroboration and the subsequent oxidation of the formula LXXIV compound are as described in the art, for example, Sweifel et al., and Knights et al., above cited. See also Brown et al, J.Am. Chem. Soc. 96, 7765 (1974).

The second step of this synthesis is the formation of the sulfonic acid ester of the primary alcohol (9-$CH_2OH$) resulting from the hydroboration-oxidation. This step is carried out as is known in the art for the formation of sulfonic acid esters using sulfonyl halides within the scope of $R_5SO_2X$ wherein $R_5$ and $X$ are as defined above. For this step the use of methanesulfonyl chloride is especially preferred, its use yielding the methanesulfonic acid ester.

The final step of this synthesis is the removal or desilylation of the protective silyl groups of the sulfonic acid ester prepared by the preceding step. This is accomplished as described above for the earlier desilylation reaction, namely contacting the sulfonic acid ester with an appropriate acid, for example, aqueous solutions of citric acid or phosporic acid, especially the latter when the silyl group is triphenylsilyl.

Finally, the transformation of sulfonic acid ester intermediate LXXV to cyclic ether LXXVI is carried out by reaction of the formula LXXV compound with a base.

Useful bases for this purpose are alkali metal hydroxides, alkoxides, or hydrides, especially wherein the alkali metal is sodium or potassium. When it is desired that the formula LXXVI compound be a fre acid, i.e. $R_1$ is hydrogen, it is advantageous to use aqueous solutions of sodium or potassium hydroxides as bases, said solutions containing sufficient of a water miscible liquid diluent, e.g., methanol or ethanol, to give a homogeneous reaction mixture. When the formula LXXV compound is an ester, it is desired that the formula LXXVI be the same ester, it is preferred to use a sodium or potassium alkoxide in an inert organic diluent, e.g., tetrahydrofuran, said alkoxide containing the same alkyl moiety as formula LXXV ($R_1$), or to use sodium or potassium tert-butoxide, also in an inert organic diluent. At least two molecular equivalents of the base per molecular equivalent of formula LXXV compound is used for this reaction. The reaction is advantageously carried out in the range about 10° to about 50° C., preferably at about 25° C., preferably in the absence of atmospheric oxygen. The formula LXXVI cyclic ether is isolated by procedures known in the art and exemplified hereinafter.

Thereafter the formula LXXVI compound is transformed to a corresponding formula LXXVI 15-deoxygenated compound by a two step chemical synthesis.

The first of these two steps requires the transformation of the formula LXXVI secondary alcohol to a corresponding 15-bromo compound. Methods known in the art for this transformation are employed. For example, see J. Hoos, et al., Canadian Journal of Chemistry 46, 86 (1968). Accordingly, the formula LXXVI compound is treated with two molecular equivalents of carbon tetrabromide and a trialkyl phosphine (e.g. tri-n-octylphosphine). The resulting reaction formation of the 15-bromide is rapid and proceeds conveniently at ambient temperatures.

The second step of this transformation involves the reduction of the bromide formed in the first step, yielding the formula LXXVII product. For this reduction sodium, potassium, or lithium borohydride is employed in an aprotic polar solvent (e.g. dimethylsulfoxide). The reaction is run for convenience at ambient temperature and is ordinarily complete within one-half to 10 hr.

Chart E provides a method whereby the formula LXXXI compound, as prepared in preceeding charts, is transformed to the formula LXXXVI, 9,11,15-trideoxy product.

The transformation of the formula LXXXI PGA-type compound to the formula LXXXII 11-hydroxymethyl compound involves a photochemical addition of methanol to the endocyclic carbon-carbon double bond of the formula LXXXI reactant. This reaction is carried out by methods known in the art for the 1,4-addition of alchols to $\alpha,\beta$-unsaturated carbonyl compounds. See, for example, Pfau et al., et al., Compt. Rend. 254, 1817 (1962) and Fraser-Reid et al., J.C.S. Chem. Commun. 1286 (1972). For this reaction, light and a sensitizer are needed. Benzophenone is a suitable sensitizer, but other sensitizers as known in the art are also useful for this purpose. Light of 3,500 A is preferable for this reaction but other wavelengths, are also useful for this purpose. It is preferred to use at least about one molecular amount of the sensitizer per molecular amount of the formula LXXXI reactant. A mixture containing a major amount of the desired 11-alpha compound of formula LXXXII and a lesser amount of the corresponding 11-beta isomer is usually obtained, the 11-alpha compound being separated from the 11-beta isomer by methods known in the art, for example, by chromatography. The desired 11-alpha product is usually more polar than the 11-beta isomer. The 11-alpha isomer is also distinguished from the 11-beta isomer on the basis of optical rotatory dispersion and circular dichroism measurements. The 11-alpha isomer will have a more negative Cotton effect than the 11-beta isomer. The intermediate of formula LXXXII is transformed to the intermediate formula LXXXIII compound by reduction of the 9-oxo atom of formula LXXXII to the 9-hydroxy group. For this transformation, any reducing agent can be used which will reduce a ketonic carbonyl group to a secondary hydroxy without also reducing carbon-carbon double bonds or the carboxylate moiety. It should be noted, however, that the desired formula LXXXIII intermediate has the 9-hydroxy in alpha configuration. Many of the known carbonyl reducing agents, for example, sodium borohydride, are relatively non-selective in producing hydroxy groups of both alpha and beta configuration when reducing a ring carbonyl group. Although these $9\alpha$ and $9\beta$ hydroxy compounds are usually separated easily by methods known in the art, for example, by chromatography, it is preferred to use for this carbonyl reduction a reducing agent which results in formation of a major amount of the desired alpha isomer, and preferably a reducing agent which gives substantially complete reduction to the alpha isomer. One such preferred carbonyl reducing agent is lithium perhydro-9b-boraphenalylhydride. See, for example, Brown et al., J. Am. Chem. Soc. 92, 709 (1970). Procedures for using this particular reducing agent and other carbonyl reducing agents are known in the art.

The formula LXXXIII compound is transformed to the corresponding sulfonic acid ester of formula LXXXIV wherein $R_5$ is a non-reactive organic radical. This is accomplished by the usual method for transforming hydroxy compounds to sulfonic acid esters, namely the reaction of the formula LXXXIII intermediate with the corresponding sulfonyl chloride or bromide, $R_5SO_2X$, in the presence of a basic tertiary amine. Any sulfonyl chloride or bromide with a non-reactive $R_5$ moiety is useful in this reaction. By "non-reactive $R_5$ moiety" is meant a moiety such that no part of said moiety itself reacts with any portion of the formula LXXXIII reactant, and such that no part of said moiety interferes with the subsequent transformation of the formula LXXXIV sulfonic acid ester to the formula LXXXV cyclic ether. Especially preferred for this reaction are arylsulfonyl halides, especially the chlorides, wherein the aryl moiety is non-reactive itself and contains a single benzene ring directly attached to the sulfur of the $SO_2X$ moiety of $R_5SO_2X$ or a sulfonyl halide of similar reactivity toward primary hydroxyl groups. Especially preferred for this reaction is p-toluenesulfonyl chloride. By using a sulfonyl halide of such reactivity, undesired reaction with the 15-hydroxy of the formula LXXXIII is minimized. It is also preferred that no more than one molecular equivalent of the sulfonyl halide be used per molecular equivalent of the formula LXXXIII compound. The remaining transformations of Chart E (LXXXIV to LXXV to LXXXVI) proceeds by the methods described in Chart D for analogous transformations (i.e., LXXV to LXXVI to LXXVII).

Chart F provides a method whereby the formula XCI compound prepared according to Charts D and E is transformed to the formula XCII 2-decarboxy-2-hydroxymethyl compound. This transformation proceeds by methods known in the art for reducing prostaglandins to corresponding primary alcohols. Thus, for example, when the formula XCI compound is an acid or ester, the reduction proceeds with lithium aluminum hydride or dissobutyl aluminum hydride.

Useful reaction diluents include diethyl ether, tetrahydrofuran, dimethoxyethane, or like organic solvents. The reaction mixture is conveniently carried out temperatures of about −78° to 100° c., although preferably at about 0°–25° C.

When the formula XCI compound is an acid, reducing agents such as diborane are also employed, when double bond reduction is not a problem.

Chart G provides a method whereby the formula CI compound, prepared above, is transformed to the various 2-decarboxy-2-aminomethyl or 2-decarboxy-2-(substituted amino)methyl-9,11,15-trideoxy-PGF-type compounds of formulas CIV, CVI, CVII, CVIII, CIX, or CX.

By the procedure of Chart G the formula CI compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type amide or formula CV PG-type, azide.

For preparation of the $PGF_{2\alpha}$ -type, amide (formula CIII) the formula CII mixed acid anhydride is reacted with liquid ammonia or ammonium hydroxide.

Alternatively, the formula CIII compound is prepared from the formula CI free acid by methods known in the art for transformation of carboxy acids to corresponding carboxyamides. For example, the free acid is transformed to a corresponding methyl ester (employing methods known in the art; e.g., excess ethereal diazomethane), and a methyl ester thus prepared is transformed to the formula CIII amide employing the methods described for the transformation of the formula CII mixed acid anhydride to the formula CIII amide.

Thereafter the formula CIV 2-decarboxy-2-aminomethyl-$PGF_{2\alpha}$ - or 11-deoxy-$PGF_{2\alpha}$ -type compound is prepared from the formula CIII compound by carbonyl reduction. Methods known in the art are employed in this transformation. For example, lithium aluminum hydride is conveniently employed.

The formula CII compound is alternatively used to prepare the formula CV azide. This reaction is conveniently carried out employing sodium azide by methods known in the art. See for example, Fieser and Fieser, Reagents for Organic Synthesis vol. 1, pgs, 1041–1043, wherein reagents and reaction conditions for the azide formation are discussed.

Finally, the formula CVI urethane is prepared from the formula CV azide by reaction with an alkanol, aralkanol, phenol, or substituted phenol. For example, when methanol is employed the formula CVI compound is prepared wherein $R_1$ is methyl. This formula CVI PG-type product is then employed in the preparation of either the formula CVII or CVIII product.

In the preparation of the formula CVII primary amine from the formula CVI urethane, methods known in the art are employed. Thus, for example, treatment of the formula CVII urethane with strong base at temperatures about 50° C. are employed. For example, sodium potassium or lithium hydroxide is employed.

Alternatively, the formula CVI compound is employed in the preparation of the formula CVIII compound. Thus, when $L_2$ is alkyl the formula CVIII compound is prepared by reduction of the formula CVI urethane wherein $R_1$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) with an alkyl chloroformate. The reaction thus proceeds by methods known in the art for the preparation of carbamates from corresponding secondary amines. Finally, the formula CX product wherein $L_2$ and $L_3$ are both alkyl is prepared by reduction of the formula CIX carbamide. Accordingly, methods hereinabove described for the preparation of the formula CVIII compound from the formula CVI compound are used. Optionally, the various reaction steps herein are proceeded by the employment of blocking groups according to $R_{10}$, thus necessitating their subsequent hydrolysis in preparing each of the various products above. Methods described hereinabove for the introduction and hydrolysis of blocking groups according to $R_{10}$ are employed.

Finally, the processes described above for converting the formula CII compound to the formula CV compound and the various compounds thereafter, result in shortening the 8α-side chain of the formula CI compound by one carbon atom. Accordingly, the formula CI starting material should be selected so as to compensate for the methylene group which is consumed in the steps of the above synthesis. Thus, where a 2a-homo-product is desired a corresponding formula CI 2a,2b-dihomo starting material must be employed. Starting materials containing an additional methylene group in the formula CI compound between the $Z_1$ moiety and the carboxyl are prepared by methods known in the art or procedures described above. For example, Wittig reagents containing an additional methylene are known in the art or prepared by methods described above.

As discussed above, the processes herein described lead variously to carboxylic acids ($R_1$ is hydrogen) or to esters when preparing novel analogs wherein $X_1$ is —$COOR_1$.

When the alkyl ester has been obtained and an acid is desired, saponification procedures, as known in the art for PGF-type compounds are employed.

For alkyl esters enzymatic processes for transformation of esters to their acid forms may be used by methods known in the art when saponification procedures would case undesired molecular changes in the prostaglandin analog. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl cyclopentyl cyclopentylm iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid PG-type compounds, differing as to yield and purity of product.

Thus by one method, the PG-type compound is converted to a tertiary amine salt, reacted with pivaloyl halide to give the mixed acid anhydride and then reacted with the aromatic alcohol. Alternatively, instead of pivaloyl halide, an alkyl or arylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Ragents for Organic Synthesis," pp. 231–236, John Wiley and Sons, Inc., New York, (1967). The PG-type compound is contacted with one to ten molar equivalents of the aromatic alcohol in the presence of 2–10 molar equivalents of dicyclohexylcarbodiimide in pyridine as a solvent.

One preferred novel process for the preparation of these esters, however, comprises the steps:
 a. forming a mixed anhydride with the PG-type compound and isobutylchloroformate in the presence of a tertiary amine and
 b. reacting the anhydride with an appropriate aromatic alcohol.

The mixed anhydride described above is formed readily at temperatures in the range −40° to +60° C., preferably at −10° to +10° C. so that the rate is reasonably fast and yet side reactions are minimized. The isobutylchloroformate reagent is preferably used in excess, for example 1.2 molar equivalents up to 4.0 per mole of the PG-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the coformed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible nonsolvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-misible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i,e., an alkanoic acid of two to 8 carbon atoms, inclusive. For example, use of acetic anhydride gives the corresponding acetate. Similar use of propionic anhydride, isobutyric anhydride, or hexanoic anhydride gives the corresponding carboxyacylate.

DESCRIPTION OF THE PREFERRED EMBODIMENTS

The invention can be more fully understood by the following examples and preparations All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, and T-60 spectrophotometer on deuterochloroform solutions with tetramethylsilane as an internal standard (downfield).

Mass spectra are recorded on an CEC model 21-110B Double Focusing High Resolution Mass Spectrometer or an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine," herein, refers to an aqueous saturated sodium chloride solution.

The A-IX solvent system used in thin layer chromatography is made up from ethyl acetate-acetic acidcyclohexane-water (90:20:50:100) as in M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone. Preparation 1 cis-4,5-Didehydro-17-phenyl-18,19,20-trinor-14-chloro-PGE$_1$ (Formula XXXVIII: Z$_2$is cis-CH$_2$-CH=CH-(CH$_2$)$_2$-; Y$_2$ is trans—CH=C Hal-; Hal is Cl; Ris hydrogen; M$_9$ is

R$_3$ and R4 of the L$_1$ moiety are hydrogen and R$_7$ is benzyl).

Refer to Chart A.

A. A solution of 24.3 g. of thallous ethoxide in 125 ml. of dry benzene is cooled in an ice bath, and thereafter a solution of 25.3g. of dimethyl-12-oxo-4-phenylbutyl phosphonate in 75 ml. of benzene is added and thereafter rinsed with 50 ml. of benzene. The solution is stirred for 30 min. at 50° C. and thereafter 22.1 g. of crystalline 3α-benzoyloxy-5α-hydroxy-2β-carboxaldehyde-1α-cyclopentaneacetic acid, γ-lactone (Formula XXI) is added rapidly. This reaction mixture is then stirred for 13 hrs. at ambient temperature yielding a brown solution of pH 9-10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding crude formula XXII product, which is then chromatographed on 600 g. of silica gel packed in 20 percent ethyl acetate i cyclohexane. Elution, collecting 500 ml. fractions, with 2 l. of 20 percent, 2 l. of 25 percent, and 4 l. of 30 percent ethyl acetate in cyclohexane yields purified product, 3α-benzoyloxy-5α-hydroxy-2β-(3-oxo-5-phenyl-trans-1-pentenyl-1α-cyclopentaneacetic acid, γ-lactone.

Alternatively this product is prepared by adding 3α-benzoyloxy-2β-carboxaldehyde-5α-hydroxy-1α-cyclopentaneacetic acid γ-lactone (3 g.) in 30 ml. of dichloromethane to a solution of dimethyl 2-oxo-(4-phenylbutylphosphonate) (6.69 g.) and sodium hydride (1.35 g.) in 15 ml. of tetrahydrofuran. The resulting reaction mixture is then stirred for 2 hrs. at about 25° C., acidified with acetic acid, and concentrated under reduced pressure. The residue is partitioned between dichloromethane and water, and the organic phase is concentrated. The residue is chromatographed on silica gel, eluting with ethyl acetate in Skellysolve B (1:1).

B. A solution of the reaction product of part A of this example (1.15 g.) in dioxane (35 ml.) is treated with N-chlorosuccinimide (9.7 g.) and stirred for 6 days. The resulting solution is then diluted with methylene chloride, washed with saline and a sodium sulfate solution, dried, and evaporated to yield a residue. The residue in benzene is subjected to silica gel chromatography, eluting with hexane and ethyl acetate (9:1) whereupon pure 3α-benzoyloxy-5α-hydroxy-2β-(1,2-dichloro-3-oxo-4-phenylpentyl)-1α-cyclopentaneacetic acid γ-lactone is recovered (as a mixture of isomers). Thereafter the dichlorides so obtained are diluted with pyridine (20 ml.) and heated at 100° C. for 4.5 hr. The resulting solution is then diluted with diethyl ether and washed with ice cold dilute hydrochloric acid and brine. The resulting mixture is then dried and subjected to silica gel chromatography, eluting with hexane and ethyl acetate (9:1), yielding pure formula XXIII product (Y$_2$ is trans—CH=CCl—) product.

Alternatively, the reaction product of part A above (0.190 g.) in dry pyridine (5 ml.) at 0° C. is treated with freshly distilled sulfuryl chloride (0.386 g.) and the reaction is maintained for 5 hr. Thereafter additional sulfuryl chloride (0.667 g.) and pyridine (5 ml.) is added and the reaction continued for 12 hr. for ambient temperature. The resulting solution is then diluted with methylene chloroide, washed with ice cold phosphoric acid, sodium bicarbonate, dried, and evaporated. The residue is chromatographed on silica gel eluting with hexane and ethyl acetate (9:1). Pure product identical with that recovered in the preceding paragraph is obtained.

C. Sodium borohydride (0.92 g.) is slowly added to a stirred suspension of 2.1 g. of anhydrous zinc chloride in 45 ml. of the dimethyl ether of ethylene glycol (glyme) with ice bath cooling. The mixture is stirred for 20 hr. at ambient temperature and thereafter cooled to −18° C. A solution of 0.76 g. of 3α-benzoyloxy-5α-hydroxy-2β-(2-chloro-3-oxo-4-phenyl-trans-1-pentenyl)-1α-cyclopentaneacetic acid γ-lactone (prepared according to part B) in 12 ml. of glyme is added over a period of 20 min. Stirring is continued for 24 hr. at −20° C. and thereafter 40 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield crude product, which when chromatographed on 120 g. of silica gel eluting with hexane and in ethyl acetate (3:1) yields the epimerically pure (15R) or (15S) formula XXIV product.

D. A solution of 100 mg. of the reaction product of part C in 20 ml. of methanol is purged with nitrogen. Thereafter, potassium carbonate (30 mg.) is added and the resulting mixture is stirred at ambient temperature until thin layer chromatographic analysis shows the solvolysis to be complete (about 12 hr.). The solution is then diluted with ice water and neutralized with cold, dilute phosphoric acid. The resulting mixture is then dried and evaporated under reduced pressure. The residue is then chromatographed using silica gel eluting with hexane and ethyl acetate (3:2). Accordingly, the deacylated formula XXV lactone is prepared.

E. A solution of 0.39 g. of the reaction product of part D above, in 25 ml. of methylene chloride (containing 1.2 ml. of dihydropyran and 1.2 mg. of pyridine hydrochloride is allowed to stand for one hr. at ambient temperature. Additional dihydropyran (1.2 ml.) is added and the reaction continued for 36 hr. The reaction mixture is then washed with water, aqueous sodium bicarbonate, dried, and evaporated, yielding the formulla XXVI bistetrahydropyranyl lactone corresponding to the lactone reaction product of part A above.

F. A solution of the reaction product of part E above (0.39 g.) in 10 ml. of toluene is cooled to −70° C. and thereafter 10 ml. of 10 percent diisobutylaluminum hydride (1.65 mmoles) in toluene (10 ml.) is slowly added. The reaction mixture is then stirred at −70° C. until thin layer chromatographic analysis indicates that the reduction is complete (about 10 min.). Thereafter the cooling bath is removed and 9 ml. of a mixture of tetrahydrofuran and water (3:1) is added slowly. The reaction mixture is then stirred and allowed to warm to room temperature, and is then filtered through a cellulose bed. The filter cake is rinsed with benzene, combined organic extracts are then dried and evaporated to yield the formula XXVII lactol.

G. A suspension of methoxymethyltriphenylphosphonium chloride (32.5 g.) in 150 ml. of tetrahydrofuran is cooled to −15° C. To the suspension is added 69.4 ml. of n-butyllithium in hexane (1.6 molar) in 45 ml. of tetrahydrofuran. After 30 min. there is added a solution of the reaction product of part F, 3α,5α-dihydroxy-2β-[2-chloro-(3R)-3-hydroxy-5-phenyl-trans-1-pentyl]-1α-cyclopentaneacetaldehyde γ-lactol bis-(tetrahydropyranyl)ether, (10 g.), in 90 ml. of tetrahydrofuran. The mixture is stirred for 1.5 hr. while warming to 25° C. The resulting solution is thereafter concentrated under reduced pressure. The residue is acidified and partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXVIII product are combined.

H. The reaction product of part G above in 20 ml. of tetrahydrofuran is hydrolyzed with 50 ml. of 66 percent aqueous acetic acid at about 57° C. for 2.5 hr. The resulting mixture is then concentrated under reduced pressure. Toluene is added to the residue and the solution is again concentrated. Finally the residue is subjected to chromatography on silica gel, eluting with chloroform and methanol (6:1). The formula XXIX γ-lactol is thereby obtained by combining and concentrating fractions as shown by thin layer chromatography to contain pure product.

I. Silver oxide is prepared by the addition of silver nitrate (1.14 g.) in water (3 ml.) dropwise to a 2 N sodium hydroxide solution (6.8 ml.). A precipitate is formed. Added to the precipitate in ice water bath is the γ lactol of part H above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol), (9:1), impurities are removed by filtration. The filtrate is then extracted with diethyl ether. The aqueous layer is then chilled in an ice bath and acidified with 10 percent potassium bisulfite solution to pH less than 2. This aqueous mixture is then extracted with diethyl ether. The ethereal extracts are then combined, washed with brine, dried over magnesium sulfate, filtered, and evaporated under reduced pressure to yield the formula XXX lactone.

J. The formula XXX lactone prepared in part 1 above is then transformed to its formula XXXI bix-tetrahydropyranyl ether derivative following the procedure described in part E.

K. The formula XXXI compound prepared in part J above is then reduced to the corresponding γ lactol bistetrahydropyranyl ether by the procedure described in part F.

L. 3-Carboxypropyltriphenylphosphonium bromide (prepared by heating 4-bromobutyric acid and triphenylphosphine in benzene at reflux for 18 hr., and thereafter purifying), 10.6 g., is added to sodiomethylsulfinylcarbanide prepared from sodium hydride (2.08 g., 57 percent) and 30 ml. of dimethylsulfoxide. The resulting Wittig reagent is combined with the formula XXXII lactol ($n$ is 2) of part K above and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate. Those fractions shown to contain the formula XXXV cis-4,5-didehydro-PGF$_{1\alpha}$ compound by thin layer chromatography are combined to yield pure product.

M. A solution of cis-4,5-didehydro-17-phenyl-18,19,20-trinor-14-chloro-PGF$_{1\alpha}$ , 11,15-bis-tetrahydropyranyl ether, prepared in Part L above, in 60 ml. of acetone is cooled to −25° C. Thereupon 1.9 ml. of Jones reagent is added. The reaction mixture is then stirred for 25 min. at −25° C. and isopropyl alcohol (1.9 ml.) is added after an additional 15 min. at −25° C. the reaction mixture is diluted with 200 ml. of water (0° C.) and extracted with diethyl ether. Ethereal extracts are washed with 150 ml. of brine, dried over magnesium sulfate, and evaporated, thereby yielding cis-4,5-didehydro-17-phenyl-18,19,20-trinor-14-chloro-PGE$_1$, 11,15-bis-tetrahydropyranyl ether, a formula XXXVII compound.

N. A solution of the crude product of part M above is reacted with 16 ml. of tetrahydrofuran, water, and acetic acid (1:3:6) and allowed to stand at 40° C. for 4 hr. The resulting mixture is thereafter diluted with 120 ml. of water and freeze dried.

The crude product is chromatographed on 25 g. of silica gel packed in 5 percent acetone in methylene chloride. Elution with 5 to 40 percent acetone in methylene chloride yields the pure formula XXXVIII title product. Preparation 2 5,6-Didehydro-PGE$_2$, methyl ester (Formula XLVII: $Z_5$ is —C ≡ C—(CH$_2$)$_3$—, $Y_1$ is trans—CH=CH—, $R_3$ and $R_4$ of the $L_1$ moiety are hydrogen, $R_1$ is methyl, $R_7$ is n-butyl, and $M_8$ is

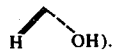

Refer to Chart B.

A. PGF$_{2\alpha}$, methyl ester (formula XLI, 4.56 g.) and 20 ml. of pyridine is subjected to dropwise addition of 4.0 g. of benzoyl chloride. The reaction mixture is then stirred at 25° C. for 16 to 24 hr. The reaction mixture is then cooled to 0° C., adding 5 ml. of water, stirring for 10 min., and thereafter extracting with diethyl ether. The ethereal layers are then washed with sodium bisulfate, sodium bicarbonate, and brine; dried over anhydrous magnesium sulfate; filtered; and concentrated under reduced pressure to yield crude formula XLII tribenzoate which is purified by high pressure liquid chromatography.

B. The reaction product of part A (5.9 g.) and 5 mg. of potassium carbonate are dissolved in 200 ml. of chloroform stirring under a nitrogen atmosphere at −20° C. Thereafter 1.6 g. of bromine in 10 ml. of chloroform is added over a period of 10 min. The reaction mixture is stirred for an additional 15 min. and concentrated under reduced pressure. The product thus obtained (the 5,6-dibromo-derivative of the tribenzoate starting material is then reacted in a solution containing 15.2 g. of 1,5-diazobicyclo-[5.4.0]-undec-5-ene (DBU) in 40 ml. of dioxane at 100° C. The reaction is maintained under a nitrogen atmosphere for 7 hr. and thereafter cooled to 25° C. for an additional 16 hr. The resulting mixture is then acidified with sodium bisulfate and extracted with 2 l. of diethyl ether. The ethereal layer is then washed with sodium bisulfate, sodium bicarbonate, and brine, and dried over anhydrous magnesium sulfate. Concentrations under reduced pressure yields crude formula XLIII 5,6-didehydro-PGF$_{2\alpha}$, methyl ester, tribenzoate.

C. The crude product of part B is placed in a solution of 250 ml. of 2 percent potassium carbonate in methanol and stirred at 25° C. for 24 hr. The resulting mixture is then acidified to pH 4 or 5 with sodium bisulfate and concentrated to a residue which is extracted with ethyl acetate. The ethyl acetate extracts are then washed with brine and dried over anhydrous magnesium sulfate. The resulting mixture is then concentrated under vacuum with excess ethereal diazomethane added to esterify a partially hydrolyzed free acid. This product is then purified by high pressure liquid chromatography using ethyl acetate and chloroform (2:1) as solvent, yielding 5,6-didehydroPGF$_{2\alpha}$, methyl ester, formula XLIV.

D. The methyl ester of part D (439.2 mg.) in 1.2 ml. of dimethylformamide are cooled to 0°–5° C. and thereafer 450 mg. of t-butyldimethylsilane and 408 mg. of imidazole in 120 ml. of dimethylformamide is added. This mixture is allowed to stand for 24 hr. at 0°–5° C. The mixture is then stirred with addition of 1 to 2 ml. of water. After 10 min. the resulting mixture is extracted with diethyl ether and hexane (1:1). The organic layer is washed with sodium bisulfate, and brine and dried over anhydrous magnesium sulfate. Concentration under reduced pressure yields crude product. Chromatography yields pure formula XLV bis-(tbutyldimethylsilyl ether) product.

E. 618 mg. of pyridine and 10 ml. of methylene chloride are combined with 390 mg. of chromic acid which mixture is then stirred for 15 min. Thereafter the reaction product of part D (385 mg.) in 3.5 ml. of methylene chloride is added and stirring is continued for one hr. The layers are then separated and a tar-containing layer is washed well with diethyl ether, and these combined ethereal layers are then washed with sodium bisulfate, sodium bicarbonate, and brine and dried over anhydrous sodium sulfate. Filtration and concentration under vacuum yields crude 5,6-didehydro-PGE$_2$, 11,15-bis-(t-butyldimethylsilyl ether), methyl ester (formula XLVI).

F. The crude product from part E is hydrolyzed in 6.5 ml. of a mixture of tetrahydrofuran water and trifluoroacetic acid (8:2:1) at 25° C. After 7 hr. the reaction mixture is neutralized by addition of saturated sodium bicarbonate (adjusted to pH 7 or 8) and is stirred for 30 min. at 25° C. The reaction mixture is then extracted with chloroform and the chloroform extract is washed with sodium bicarbonate and brine and dried over anhydrous magnesium sulfate. Concentration under reduced pressure yields crude formula XLVII title product, which is then purified using preparative thin layer chromatography (chloroform and acetone 2:1). Preparation 3 3,7-inter-m-phenylene-3-oxa-16-phenoxy-4,5,6,17,18,19,20-heptanor-PGE$_1$ or PGA$_1$ (Formula LX or LXV: $R_1$ is hydrogen, $Z_3$ is oxa, $Y_1$ is trans—CH=CH—, $R_3$ and $R_4$ of the $L_1$ moiety are hydrogen and $R_7$ is phenoxy, $M_9$ is

and g is one).

Refer to Chart C.

A. 3,7-inter-m-phenylene-4,5,6-trinor-PGF$_{1\alpha}$, methyl ester (10 g.) in 200 ml. of methanol is cooled to 0° C. in an ice-bath. A stream of ozone, generated from a conventional ozone-producing apparatus, is passed through the mixture until the starting material is completely consumed. Thereupon, the resulting mixture is washed and concentrated, and the residue chromatographed, yielding pure formula LII aldehyde.

B. Following the procedure of Preparation 2, part A, the reaction product of part A above is transformed to the formula LIII dibenzoate.

C. Following the procedure of Preparation 1, part A, but employing dimethyl 2-oxo-3-phenoxypropylphosphonate, the reaction product of part B above, is transformed to the formula LIV compound.

D. Following the procedure of Preparation 1, part C, the reaction product of part C above is transformed to a formula LVI compound.

E. Following the procedure of Preparation 2, part C, the reaction product of part D above is transformed to a formula LVII compound.

F. Following the procedure of Preparation 2, part D, the reaction product of part E above is transformed to a formula LVIII compound.

G. Following the procedure of Preparation 2, part E, the reaction product of part F above is tranformed to a formula LIX compound.

H. Following the procedure of Preparation 2, part F, the reaction product of part G above is transformed to a formula LX PGE-type title compound.

I. To a stirred solution of the reaction product of part H above in 3.3 ml. of dry pyridine at ambient temperature under a nitrogen atmosphere is added one ml. of acetic anhydride. After 2.5 hr. the reaction mixture is cooled to 0° C. and 3.3 ml. of methanol are added. The reaction mixture is then stirred for 5 min. at 0° C. and for 18 hr. at ambient temperature. The reaction is then quenched by addition of an equilibrated mixture of sodium bisulfate, ice, and diethyl ether. The aqueous extract ct is then washed well with diethyl ether and the organic extract is combined, washed with water, saturated sodium bicarbonate, and brine. The resulting mixture is thereafter dried over sodium sulfate and evaporated to yield the formula LXI 11,15-diacetate.

J. Crude reaction product of part I above is chromatographed on silica gel packed in ethyl acetate, eluting with 50 percent ethyl acetate and hexane. Fractions shown to contain pure formula LXII compound by thin layer chromatography are combined.

K. To a solution of the reaction product of step J above, dissolved in methanol, there is added the esterase powder described in U.S. Pat. No. 3,761,356 at temperature for several days. The resulting mixture is then acidified with 3N hydrochloric acid and concentrated to an aqueous residue. The residue is diluted with 25 ml. of water and extracted with diethyl ether. The combined extracts are then washed with brine, dried, and concentrated. The residue is then chromatographed on silica gel, yielding pure formula LXV product, a free acid.

Following procedures generally described in Preparations 1-3, but employing appropriate starting material and reactants, there are prepared each of the various formula LXXI PGE-type compounds, or their corresponding 14-chloro analogs, except those wherein $Z_1$ is $-CH_2-O-CH_2-(CH_2)_g-CH_2-$. These compounds, the 5-oxa-PGE-type formula LXXI compounds, are obtained by methods described in U.S. Pat. No. 3,864,387.

Preparation 4 cis-4,5,13,14-Tetradehydro-17-phenyl-18,19,20-trinor-$PGE_1$ (Formula XXXIX: $Z_2$, $R_1$, $M_9$, $L_1$, and $R_7$ are as defined in Preparation 1).

Refer to Chart A.

A. The reaction product of part L of Preparation 1, cis-4,5-didehydro-14-chloro-17-phenyl-18,19,20-trinor-$PGF_{1\alpha}$, 11,15-bis-tetrahydropyranyl ether, is deetherified following the procedure of part N of Preparation 1.

B. The reaction product of part A above in dimethylsulfoxide is treated with 0.5 M potassium tert-butoxide in dimethylsulfoxide. Silver nitrate impregnated silica gel thin layer chromatography is used to monitor the progress of the reaction. After several hr., the reaction being complete, cis-4,5,13,14-tetradehydro-17-phenyl-18,19,20-trinor-$PGF\alpha$ is isolated.

C. Following the procedure of Example 2, parts D, E, and F the reaction product of part B above is transformed to cis-4,5,13,14-tetradehydro-17-phenyl-18,19,20-trinor-$PGE_1$.

D. Following the procedure of Preparation 3, parts I, J, and K, but employing the reaction product of part C above, there is prepared the title product, cis-4,5,13,14-tetradehydro-17-phenyl-18,19,20-trinor-$PGA_1$.

Preparation 5 5,6-Didehydro-$PGA_2$, methyl ester (Formula XLVIII: $Z_5$, $Y_1$, $L_1$, $M_9$, $R_1$, and $R_7$ are as defined in Preparation 2).

Refer to Chart B.

Following the procedure of Preparation 3, parts I, J, and K, the reaction product of Preparation 2 is transformed to the title product.

Preparation 6 cis-4,5-13,14-Tetradehydro-17-phenyl-18,19,20-trinor-9-deoxy-9-methylene-$PGF_2$, methyl ester (Formula LXXIV: $R_1$ is methyl, $Z_1$ is cis—$CH_2$—CH=CH—$(CH_2)_2$—, $Y_1$ is —C ≡ C—, $R_3$ and $R_4$ of the $L_1$ moiety, are hydrogen, $M_9$ is

and $R_7$ is benzyl).

Refer to Chart D.

A. A solution of the methyl ester of Preparation 1 (300 mg., prepared by ethereal diazomethane esterification) in 15 ml. of tetrahydrofuran, containing 3 ml. of hexamethyldisilizane and 0.75 ml. of trimethylchlorosilane is stirred at ambient temperature for about 5 hr. Following removal of solvents under reduced pressure, the residue is taken up in 50 ml. of xylene, filtered through Celite, and concentrated under reduced pressure to yield a 14-chloro analog of a compound of formula LXXII.

B. A tetrahydrofuran solution of methyl magnesium chloride (50 ml.; 2M) is added dropwise during 20 min. to a stirred solution of N,S-dimethyl-S-phenylsulfoximine (17 g.) in 150 ml. of anhydrous tetrahydrofuran at 0° C. The resulting mixture is then stirred for 15 min. at 0° C. and is thereafter maintained at 0° C. being added to a stirred solution of the reaction product of part A (18 g.) and 65 ml. of tetrahydrofuran at about −78° C. Addition continues over about 35 min. Stirring is continued at −78° C. for 2.5 hr. thereafter. The resulting mixture is then poured into saturated aqueous ammonium chloride (500 ml.) ice, and diethyl ether. The resulting mixture is extracted with diethyl ether and the combined extracts are washed with brine and dried over sodium sulfate. Removal of diethyl ether under reduced pressure yields a residue which is dissolved in 200 ml. of methanol. Aqueous citric acid is then added to the methanol containing solution and the resulting mixture stirred for 30 min. at ambient temperature. Brine is added and the mixture is extracted several times with methyl acetate. The combined extracts are then washed with brine, dried over sodium sulfate, and evaporated under reduced pressure to yield a residue, The residue from the preceeding paragraph is dissolved in 900 ml. of tetrahydrofuran. To this solution is added with stirring 140 ml. of water, 140 ml. of acetic acid, and amalgamated aluminum prepared from 30 g. of 20 mesh aluminum metal granules. This mixture is maintained at about 20° to 25° C. After stirring for one hr., Celite is added, and the mixture is filtered through a pad of Celite. The filter pad is washed with three 150 ml. portions of tetrahydrofuran and the combined filtrate and washings are evaporated under reduced pressure. Brine is added to the residue and the mixture is extracted with ethyl acetate and hexane (4:6). Combined extracts are then washed with 150 ml. portions of brine and thereafter with 0.5 M aqueous disodium hydrogen phosphate until pH 9 is achieved. Then the combined extracts are washed with brine, dried over sodium sulfate and evaporated to yield a residue which is chromatographed on silica gel, yielding the 14-chloro analog of the formula LXXIII compound.

C. The reaction product of part B is transformed to the title product by dehydrohalogenation, following the procedure described in Preparation 2, part B.

Preparation 7 5,6-Didehydro-9-deoxy-9-methylene-PGF$_2$, methyl ester (Formula LXXIII: R$_1$ is methyl, Z$_1$ is —C ≡ C—(CH$_2$)$_3$—, M$_9$ is

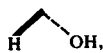

Y$_1$ is trans—CH=CH—, R$_3$ and R$_4$ of the L$_1$ moiety are hydrogen, and R$_7$ is n-butyl).

Refer to Chart D.

A. Following the procedure of Preparation 6, part A, the reaction product of Preparation 2 is silylated, yielding a formula LXXII compound.

B. Following the procedure of Preparation 6, part B, the reaction product of part A above is transformed to the title product.

Preparation 8 3,7-inter-m-phenylene-3-oxa-16-phenoxy-4,5,6,17,18,19,20-heptanor-9-deoxy-9-methylene-PGF$_1$, methyl ester (Formula LXXIII: R$_1$ is methyl, Z$_1$ is

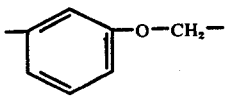

M$_9$ is

Y$_1$ is trans—CH=CH—, R$_3$ and R$_4$ of the L$_1$ moiety are hydrogen, and R$_7$ is

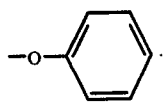

Refer to Chart D

A. The methyl ester of the title product of Preparation 3 (prepared by ethereal diazomethane esterification) is transformed to the formula LXXII 15-silyl derivative following the procedure of Preparation 6, part A.

B. Following the procedure of Preparation 6, part B, the reaction product of part A above is transformed to the title product.

Preparation 9 11-Deoxy-11α-hydroxymethyl-cis-4,5,13,14-tetradehydro-17-phenyl-18,19,20-trinor-PGF$_{1\alpha}$ (Formula LXXXIII: R$_1$ is hydrogen, Z$_1$ is cis-CH$_2$—CH=CH—(CH$_2$)$_2$—, Y$_1$ is —C ≡ C—, M$_9$ is

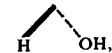

R$_3$ and R$_4$ of the L$_1$ moiety are both hydrogen, and R$_7$ is benzyl).

Refer to Chart E.

A. A solution of the title product of Preparation 4 (4.0 g.) and benzophenone (300 mg.) in 900 ml. of methanol is irradiated in a Rayonet type RS preparative photochemical reactor using a 3,500 A light. The reaction mixture is maintained at 28°–32° C., stirred, and oxygen is excluded by purging with nitrogen. After about 2.5 hr. additional benzophenone (300 mg.) is added. Then after each of two further reaction periods of one hr. additional benzophenone (300 mg.) is added. One hr. later thin layer chromatographic analysis, using the A-IX solvent system indicates starting material is completely consumed. Excess methanol is then evaporated under reduced pressure and the residue chromatographed on silica gel yielding a formula LXXXII product.

B. A solution of the reaction product of part A in 200 ml. of tetrahydrofuran is added gradually during 10 min. to 20 ml. of a stirred solution of 0.6N lithium perhydro-9b-boraphenalylhydride in diglyme at about −78° C. The resulting mixture is then stirred for 3 hr. at −78° C. and thereafter allowed to warm to 20° C. during 30 min. To the mixture is then added successively water (3 ml.), 1N hydrochloric acid (15 ml.), and additional water (300 ml.). The resulting mixture is then extracted several times with ethyl acetate and the combined ethyl acetate extracts are extracted thrice with 0.5 M aqueous sodium bicarbonate. The combined aqueous extracts are washed once with ethyl acetate, acidified with 2N aqueous potassium bisulfate and then extracted several times with ethyl acetate. Combined ethyl acetate extracts are then washed with brine, dried with anhydrous sodium sulfate, and evaporated to yield a residue which is chromatographed yielding the title product.

Preparation 10 11-Deoxy-11-hydroxymethyl-5,6-didehydro-PGF$_{2\alpha}$, methyl ester (Formula LXXXIII: R$_1$ is methyl, Z$_1$ is —C ≡ C—(CH$_2$)$_3$—, Y$_1$ is trans—CH=CH—, M$_9$ is

R$_3$ and R$_4$ of the L$_1$ moiety are both hydrogen, and R$_7$ is n-butyl).

Refer to Chart E.

A. Following the procedure of Preparation 9, the title product of Preparation 5 is transformed to 11-deoxy-11-hydroxymethyl-5,6-didehydro-PGE$_2$, methyl ester.

B. Lithium tri-(t-butoxy)-aluminumhydride (1.3 g.) is slowly added to a solution of the reaction product of part A above in 20 ml. of tetrahydrofuran. The mixture is stirred for 18 hr, at 25° C. and then concentrated under reduced pressure. Water and diethyl ether are then added to the residue and the resulting mixture acidified with 2N aqueous potassium bisulfate. The acidified mixture is then extracted with diethyl ether and the combined extracts are washed successively with aqueous sodium bicarbonate and water, dried over sodium sulfate, and evaporated to a residue. This residue is then chromatographed on silica gel yielding pure title product.

Preparation 11  11-Deoxy-11-hydroxymethyl-3,7-phenylene-3-oxa-16-phenoxy-4,5,6,17,18,19,20-heptanor-PGF$_{1\alpha}$ (Formula LXXXIII: $R_1$ is hydrogen, $Z_1$ is

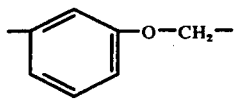

$Y_1$ is trans—CH=CH—, $M_1$ is

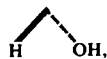

$R_3$ and $R_4$ of the $L_1$ moiety are both hydrogen, and $R_7$ is phenoxy).

Refer to Chart E.

Following the procedure of Preparation 9, the PGA$_1$-type title product of Preparation 3 is transformed to the title product.

Preparation 12  9-Deoxy-9α-mesyloxymethyl-cis-4,5,13,14-tetradehydro-17-phenyl-18,19,20-tetranor-PGF$_1$, methyl ester (Formula LXXV: $R_1$ is methyl, $Z_1$, $Y_1$, $M_9$, $L_1$, and $R_7$ are as defined in Preparation 6 and $R_5$ is methyl).

Refer to Chart E.

A. Triphenylsilane (11 g.) is added in one portion with stirring to a solution of the methyl ester of the title product of Preparation 6 (6.5 g.; prepared by ethereal diazomethane esterification) in 65 ml. of pyridine at 0° C. under a nitrogen atmosphere. The resulting mixture is then allowed to warm to about 25° C. and stirred at this temperature under nitrogen for 2 hr. Then an additional 11 g. of triphenylsilane is added and the mixture is stirred at 25° C. under a nitrogen atmosphere for about 65 hr. The resulting mixture is then poured into a mixture of water, ice, and hexane. This mixture is then extracted several times with hexane and the combined extracts are washed successively with water and ice-cold aqueous potassium bisulfate until such washes are acidic. Thereafter the resulting mixture is washed with water, aqueous sodium bicarbonate, and finally brine. This washed mixture is then dried over sodium sulfate and evaporated under reduced pressure to a residue. The residue is then chromatographed on silic gel yielding the 11,15-bis-(triphenylsilyl ether) of the initial reactant.

B. A solution of 0.5 M 9-borobicyclo-[3.3.1]-nonane in tetrahydrofuran (102 ml.) is added with stirring during 45 min. to a solution of the reaction product of part A (15 g.) in 600 ml. of tetrahydrofuran. The reaction proceeds under a nitrogen atmosphere at 0° C. with stirring. The reaction conditions are maintained for 4 hr., at which time there is added successively 16 ml. of 30 percent aqueous hydrogen peroxide (dropwise) and 20 ml. of 3N aqueous sodium hydroxide. The resulting mixture is then stirred for 6 hr. at 0° C. and thereafter diluted with brine and extracted with ethyl acetate. The combined extracts are then washed with brine, dried over sodium sulfate and concentrated to a residue. The residue is then dissolved in 600 ml. of tetrahydrofuran and to this solution at 0° C. is added 10 ml. of 30 percent aqueous hydrogen peroxide and 10 ml. of 3N aqueous potassium hydroxide. The resulting mixture is stirred 3 hr. at ambient temperature and diluted with brine and extracted with ethyl acetate. Combined extracts are then washed with brine, dried over anhydrous sodium sulfate, and evaporated under reduced pressure. The resulting residue is chromatographed yielding pure 9-deoxy-9α-hydroxymethyl-cis-4,5,13,14-tetradehydro-17-phenyl-18,19,20-trinor-PGF$_{1\alpha}$, methyl ester, 11,15-bis (triphenylsilyl ether).

C. Triethylamine is added in one portion to a solution of the reaction product of part B above of dichloromethane at 0° C. under a nitrogen atmosphere. Thereafter methanesulfonylchloride is added dropwise during one min. and the resulting mixture is stirred under the nitrogen atmosphere at 0° C. for 15 min. The resulting mixture is then poured into a mixture of ice, water, sodium bicarbonate, and hexane and this mixture extracted several times with hexane. The combined extracts are then washed successively with ice-water, dilute aqueous potassium bicarbonate, aqueous sodium bicarbonate, and brine. The washed mixture is then dried over sodium sulfate and evaporated under reduced pressure to yield 9α-mesyloxymethyl derivative of the starting materials.

D. Water (30 ml. is added to a solution of reaction product from step C (1.00 g.) in 40 ml. of tetrahydrofuran. To the resulting slurry is added one ml. of 85 percent phosphoric acid, and the mixture is heated with stirring at 40° C. for 4 hr. The mixture is allowed to stand about 15 hr. at 25° C., and is then poured into a mixture of ice and aqueous sodium bicarbonate solution. This mixture is extracted several times with ethyl acetate. The combined extracts are washed with brine, dried with anhydrous sodium sulfate, and evaporated under reduced pressure to yield the title product.

Preparation 13  9-Deoxy-9α-mesyloxymethyl-5,6-didehydro-PGF$_2$, methyl ester, (Formula LXXV: $R_1$, $Z_1$, $M_9$, $L_1$, and $R_7$ are as defined in Preparation 7 and $R_5$ is methyl).

Refer to Chart D.

Following the procedure of Preparation 12, but employing title product of Preparation 7, there is prepared the title compound.

Preparation 14  9-Deoxy-9α-mesyloxymethyl-3,7-inter-m-phenylene-3-oxo-16-phenoxy-4,5,6,17,18,19.20-heptanor-PGF$_1$, methyl ester (Formula LXXV: $R_1$, $Z_1$, $Y_1$, $M_9$, $L_1$, and $R_7$ are as defined in Preparation 8 and $R_5$ is methyl).

Refer to Chart D.

Following the procedure of Preparation 12, but employing the title product of Preparation 8, there is prepared the title product.

Following the procedures described in Preparations 1, 2, 3, 4, 5, 6, 7, 8, 12, 13, and 14, there are prepared 9-deoxy-9α-mesyloxymethyl-PGF-type compounds corresponding to each of the 9,11,15-trideoxy-11α,9α-epoxymethano-PGF-type compounds described herein.

Preparation 15  11-Deoxy-11α-tosyloxymethyl-cis-4,5,13,14-tetradehydro-17-phenyl-18,19,20-trinor-PGF$_{1\alpha}$, methyl ester (Formula LXXXIV: $R_1$ is methyl, $Z_1$, $Y_1$, $M_9$, $L_1$, and $R_7$ are as defined in Preparation 9 and $R_5$ is p-tolyl).

Refer to Chart E.

To a solution of the methyl ester of the title product of Preparation 9 (725 mg.; prepared by ethereal diazomethane esterification of the free acid) in 10 ml. of anhydrous pyridine at 0° C. p-toluenesulfonyl chloride (405 mg.) is added in one portion with stirring. The resulting mixture is then stirred at 0°–5° C. under a nitrogen atmosphere for 12 hr. and thereafter poured into a mixture of ice, water, brine, diethyl ether, and 2M aqueous potassium bisulfate (67 ml.). The resulting mixture is then shaken and extracted several times with diethyl ether and the combined extracts are washed successively with water, aqueous sodium bicarbonate, and brine. The washed mixture is then dried over sodium sulfate and concentrated under reduced pressure to a residue. This residue is then chromatographed on silica gel yielding pure title product.

Preparation 16α 11-Deoxy-11α-tosyloxymethyl-5,6-didehydro-PGF$_{2\alpha}$, methyl ester (Formula LXXXIV: $R_1$, $Z_1$, $Y_1$, $M_9$, $L_1$, and $R_7$ are as defined in Preparation 10 and $R_5$ is p-tolyl). Refer to Chart E.

Following the procedure of Preparation 15, but employing the title product of Preparation 10 in place of the starting material therein, there is prepared pure title product.

Preparation 17 11-Deoxy-11α-tosyloxymethyl-3,7-inter-m-phenylene-3-oxo-16-phenoxy-4,5,6,17,18,19,20-heptanor-PGF$_{1\alpha}$, methyl ester (Formula LXXIV: $R_1$ is methyl, $Z_1$, $Y_1$, $M_9$, $L_1$, and $R_7$ are as defined in Preparation 11 and $R_5$ is p-tolyl). Refer to Chart E.

Following the procedure of Preparation 15, but employing the methyl ester of the title product of Preparation 11 (prepared by ethereal diazomethane esterification) in place of the starting material therein, there is prepared pure title product.

Following the procedure of Preparations 1, 2, 3, 9, 10, 11, 15, 16, and 17, there are prepared 11-deoxy-11α-tosyloxymethyl-PGF$_\alpha$ -type compounds corresponding to each of the 9,11,15-trideoxy-9α,11α1-epoxymethano-PGF-type products herein.

EXAMPLE 1

9,11-Dideoxy-11α,9α-epoxymethano-cis-4,5,13,14-tetradehydro-17-phenyl-18,19,20-tetranor-PGF$_1$ (Formula LXXVI: $R_1$ is hydrogen, $Z_1$, $Y_1$, $M_9$, $L_1$, $R_7$ are as defined in Preparation 12).

Refer to Chart D.

Aqueous sodium hydroxide (3M; 2ml.) is added with stirring to a solution of the title product of Preparation 12 (95 mg.) in 10 ml. of methanol at 0° C. The mixture is then stirred for 1.5 hr. at 0° C. and thereafter an additional 2 ml. of 3 M aqueous sodium hydroxide is added. This resulting mixture is then stirred for 2 hr. at ambient temperature and thereafter poured into a mixture of brine, ice, and aqueous potassium bisulfate. The resulting mixture is then extracted several times with ethyl acetate and the combined extracts washed with brine, dried over sodium sulfate, and concentrated under reduced pressure to a residue. This residue is then chromatographed on silica gel yielding pure title product.

EXAMPLE 2

9,11-Dideoxy-11α,9α-epoxymethano-5,6-didehydro-PGF$_2$ (Formula LXXVI: $R_1$ is hydrogen, $Z_1$, $Y_1$, $M_9$, $L_1$, and $R_7$ are as defined in Preparation 13).

Following the procedure of Example 1, but employing the title product of Preparation 13 in place of the starting material therein, there is prepared title products.

EXAMPLE 3

9,11-Dideoxy-11α,9α-epoxymethano-3,7-inter-m-phenylene-3-oxa-16-phenoxy-4,5,6,17,18,19,20-heptanor-PGF$_1$ (Formula LXXVI: $R_1$ is hydrogen, $Z_1$, $Y_1$, $M_9$, $L_1$, and $R_7$ are as defined in Preparation 14).

Refer to Chart D.

Following the procedure of Example 1, but employing the title product of Preparation 14 in place of the starting material therein, there is prepared the title product.

Following the procedure of Examples 1–3 there are prepared each of the various 9,11-dideoxy-11,9-epoxmethano-PGF-type free acids corresponding to each of the various 9,11,15-trideoxy-11α,9α-epoxymethano-PGF-type products.

EXAMPLE 4

9,11-Dideoxy-9α,11α-epoxymethano-cis-4,5,13,14 -tetradehydro-17-phenyl-18,19,20-trinor-PGF$_1$ (Formula LXXXV: $R_1$ is hydrogen, $Z_1$, $Y_1$, $M_9$, $L_1$, and $R_7$ are as defined in Preparation 15).

Refer to Chart E.

The reaction product of Preparaton 15, (50 mg.) in potassium t-butoxide (22 mg.) in 5 ml. of anhydrous tetrahydrofuran is stirred under a nitrogen atmosphere at 25° C. for 60 min. The solution is then diluted with 50 ml. of diethyl ether and poured into 75 ml. of cold brine containing 5 ml. of 2N aqueous potassium bisulfate. The resulting mixture is then extracted with three 75 ml. portions of diethyl ether. The combined extracts are then washed with aqueous sodium bicarbonate solution and brine, dried over sodium sulfate, and concentrated under reduced pressure to yield a residue. The residue is then chromatographed on neutral silica gel yielding pure title product.

EXAMPLE 5

9,11-Dideoxy-9α,11α-epoxymethano-5,6-didehydro-PGF$_2$ (Formula LXXXV: $R_1$ is hydrogen, $Z_1$, $Y_1$, $M_9$, $L_1$ and $R_7$ are as defined in Preparation 16).

Refer to Chart E.

Following the procedure of Example 4, but employing the title product of Preparation 16 in place of the starting material therein, there is prepared the title product.

EXAMPLE 6

9,11-Dideoxy-9α,11α-epoxymethano-3,7-inter-m-phenylene-3-oxa-16-phenoxy-4,5,6,17,18,19,20-heptanor-PGF$_1$ (Formula LXXXV: $R_1$ is hydrogen, $Z_1$, $Y_1$, $M_9$, $L_1$, and $R_7$ are as defined in Preparation 17).

Refer to Chart E.

Following the procedure of Example 4, but employing the title product of Preparaion 17 in place of the starting material therein, there is prepared the title product.

Following the procedures of Examples 4, 5, and 6, and employing each of the various 11-deoxy-11α-tosyloxymethyl-PGF-type compounds described above, there are prepared 9,11-dideoxy-9α,11α-epoxymethano-PGF-type compounds corresponding to each of the various 9,11,15-trideoxy-9α,11α-epoxymethano-PGF-type products described above.

EXAMPLE 7

9,11,15-Trideoxy-11α,9α-epoxymethano-cis-4,5,13,14-tetradehydro-17-phenoxy-18,19,20-trinor-PGF$_1$ (Formula LXXVII: R$_1$, Z$_1$, Y$_1$, L$_1$, and R$_7$ are as defined in Example 1).

Refer to Chart D.

A. A solution of 10 g of the title product of Example 1 in 50 ml. of diethyl ether (anhydrous) is treated with 25 g. of carbon tetrabromide with stirring in an ice bath. Thereafter, 28 g. of tri-n-ocytlphosphine is added slowly, at a rate such that the diethyl ether solvent does not reflux. After about 15 min. at room temperature the mixture is diluted with 800 ml. of diethyl ether and cooled −10° C. The diethyl ether solution is then separated and concentrated under reduced pressure and the residue chromatographed on silica gel.

B. The chromatographed product from part A (about 8 g.) in 40 ml. of anhydrous dimethylsulfoxide is added dropwise over about 30 min. to a stirred suspension of 1.4 g. of sodium borohydride in 40 ml. of anhydrous dimethylsulfoxide. The reaction temperature is maintained at 15° C. After the addition is complete the resulting solution is stirred at 15°–18° C. for 3 hr. and then glacial acetic acid is cautiously added (with evolution of hydrogen gas). 800 ml. of water is then added to the resulting mixture and the mixture extracted well with diethyl ether. The combined ethereal extracts are then washed with water, saturated sodium bicarbonate, and brine. The washed mixture is then dried over sodium sulfate and concentrated under reduced pressure to a residue. This residue is then chromatograped on silica gel yielding pure title product.

Following the procedure of Example 7, but employing respectively the title products of Examples 2–6 in place of the starting material therein, there are prepared:

9,11,15-Trideoxy-11α,9α-epoxymethano-5,6-didehydro-PGF$_2$;

9,11,15-Trideoxy-11α,9α-epoxymethano-3,7-inter-m-phenylene-3-oxa-16-phenoxy-4,5,6,17,18,19,20-heptanor-PGF$_1$;

9,11,15-Trideoxy-9α,11α-epoxymethano-cis-4,5,13,14-tetradehydro-17-phenyl-18,19,20-trinor-PGF$_1$;

9,11,15-Trideoxy-9α,11α-epoxymethano-5,6-didehydro-PGF$_2$; and 9,11,15-Trideoxy-9α,11α-epoxymethano-3,7-inter-m-phenylene-16-phenoxy-4,5,6,17,18,19,20-heptanor-PGF$_1$.

Further, following the procedure of the above Examples, there are prepared methyl esters of the above 9,11,15-trideoxy-9α,11α-epoxymethano- or 11α,9α-epoxy-methano-PGF-type compounds by esterification with ethereal diazomethane.

Following the procedure of Example 1, but employing corresponding starting material as described above, there are prepared 9,11,15-trideoxy-9α,11α-epoxymethano- or 11α,9α-epoxymethano-PGF$_2$- or PGF$_1$-type compounds, in free acid or methyl ester form, which exhibit the following functional characteristics:

16-Methyl-;
16,16-Dimethyl-;
16-Fluoro-;
16,16-Difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
16-Methyl-16-phenoxy-18,19,20-trinor-;
13,14-Didehydro-; 16-Methyl-13,14-didehydro-;
16,16-Dimethyl-13,14-didehydro-;
16-Fluoro-13,14-didehydro-
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;

2,2-Difluoro-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;

Following the procedure of Example 1, but employing corresponding starting material as described above there are prepard 9,11,15-trideoxy-9α,11α-epoxymethano- or 11α,9α-epoxymethano-PGF$_1$-type compounds, in free acid of methyl ester form, which exhibit the following functional characteristics:

3,7-Inter-m-phenylene-3-oxa-4,5,6-trinor-;
3,7-Inter-m-phenylene-3-oxa-4,5,6-trinor-16-methyl-;
3,7-Inter-m-phenylene-3-oxa-4,5,6-trinor-16,16-dimethyl-;
3,7-Inter-m-phenylene-3-oxa-4,5,6-trinor-16-fluoro-;
3,7-Inter-m-phenylene-3-oxa-4,5,6-trinor-16,16-difluoro-;
3,7-Inter-m-phenylene-3-oxa-17-phenyl-4,5,6,18,19,20-hexanor-;
3,7-Inter-m-phenylene-3-oxa-17-(m-trifluoromethylphenyl)-4,5,6,18,19,20-hexanor;
3,7-Inter-m-phenylene-3-oxa-17-(m-chlorophenyl)-4,5,6,18,19,20-hexanor;
3,7-Inter-m-phenylene-3-oxa-17-(p-fluorophenyl)-4,5,6,18,19,20-hexanor-;
3,7-Inter-m-phenylene-3-oxa-16-methyl-17-phenyl-4,5,6,18,19,20-hexanor-;
3,7-Inter-m-phenylene-3-oxa-16,16-dimethyl-17-phenyl-4,5,6,18,19,20-hexanor;
3,7-Inter-m-phenylene-3-oxa-16-fluoro-17-phenyl-4,5,6,18,19,20-hexanor-;
3,7-Inter-m-phenylene-3-oxa-16,16-difluoro-17-phenyl-4,5,6,18,19,20-hexanor-;
3,7-Inter-m-phenylene-3-oxa-16-phenoxy-4,5,6,17,18,19,20-heptanor-;
3,7-Inter-m-phenylene-3-oxa-16-(m-trifluoromethylphenoxy)-4,5,6,17,18,19,20-heptanor-;
3,7-Inter-m-phenylene-3-oxa-16-(m-chlorophenoxy)-4,5,6,17,18,19,20-heptanor-;
3,7-Inter-m-phenylene-3-oxa-4,5,6-trinor-16-(p-fluorophenoxy)-4,5,6,17,18,19,20-heptanor-;
3,7-Inter-m-phenylene-3-oxa-16-phenoxy-4,5,6,18,19,20-hexanor-;
3,7-Inter-m-phenylene-3-oxa-4,5,6-trinor-16-methyl-16-phenoxy-4,5,6,18,19,20-hexanor-;
3,7-Inter-m-phenylene-3-oxa-4,5,6-trinor-13,14-didehydro-;

3,7-Inter-m-phenylene-3-oxa-4,5,6-trinor-16-methyl-13,14-didehydro-;
3,7-Inter-m-phenylene-3-oxa-4,5,6-trinor-16,16-dimethyl-13,14-didehydro-;
3,7-Inter-m-phenylene-3-oxa-4,5,6-trinor-16-fluoro-13,14-didehydro-;
3,7-Inter-m-phenylene-3-oxa-4,5,6-trinor-16,16-difluoro-13,14-didehydro-;
3,7-Inter-m-phenylene-3-oxa-17-phenyl-4,5,6,18,19,20-hexanor-13,14-didehydro-;
3,7-Inter-m-phenylene-3-oxa-17-(m-trifluoromethylphenyl)-4,5,6,18,19,20-hexanor-13,14-didehydro-;
3,7-Inter-m-phenylene-3-oxa-17-(m-chlorophenyl)-4,5,6,18,19,20-hexanor-13,14-didehydro-;
3,7-Inter-m-phenylene-3-oxa-17-(p-fluorophenyl)-4,5,6,18,19,20-hexanor-13,14-didehydro-;
3,7-Inter-m-phenylene-3-oxa-16-methyl-17-phenyl-4,5,6,18,19,20-hexanor-13,14-didehydro-;
3,7-Inter-m-phenylene-3-oxa-16,16-dimethyl-17-phenyl-4,5,6,18,19,20-hexanor-13,14-didehydro-;
3,7-Inter-m-phenylene-3-oxa-16-fluoro-17-phenyl-4,5,6,18,19,20-hexanor-13,14-didehydro;
3,7-Inter-m-phenylene-3-oxa-16,16-difluoro-17-phenyl-4,5,6,18,19,20-hexanor-13,14-didehydro-;
3,7-Inter-m-phenylene-3-oxa-16-phenoxy-4,5,6,17,18,19,20-heptanor-13,14-didehydro;
3,7-Inter-m-phenylene-3-oxa-16-(m-trifluoromethylphenoxy)-4,5,6,17,18,19,20-heptanor-13,14-didehydro-;
3,7-Inter-m-phenylene-3-oxa-16-(m-chlorophenoxy)-4,5,6,17,18,19,20-heptanor-13,14-didehydro-;
3,7-Inter-m-phenylene-3-oxa-16-phenoxy-4,5,6,18,19,20-hexanor-13,14-didehydro-;
3,7-Inter-m-phenylene-3-oxa-16-methyl-16-phenoxy-4,5,6,18,19,20-hexanor-13,14-didehydro-;
3,7-Inter-m-phenylene-3-oxa-4,5,6-trinor-13,14-dihydro-;
3,7-Inter-m-phenylene-3-oxa-4,5,6-trinor-16-methyl-13,14-dihydro-;
3,7-Inter-m-phenylene-3-oxa-4,5,6-trinor-16,16-dimethyl-13,14-dihydro;
3,7-Inter-m-phenylene-3-oxa-4,5,6-trinor-16-fluoro-13,14-dihydro-;
3,7-Inter-m-phenylene-3-oxa-4,5,6-trinor-16,16-difluoro-13,14-dihydro-;
3,7-Inter-m-phenylene-3-oxa-17-phenyl-4,5,6,18,19,20-trinor-13,14-dihydro-;
3,7-Inter-m-phenylene-3-oxa-17-(m-trifluoromethylphenyl)-4,5,6,18,19,20-hexanor-13,14-dihydro-;
3,7-Inter-m-phenylene-3-oxa-17-(m-chlorophenyl)-4,5,6,18,19,20-hexanor-13,14-dihydro-;
3,7-Inter-m-phenylene-3-oxa-17-(p-fluorophenyl)-4,5,6,18,19,20-hexanor-13,14-dihydro-;
3,7-Inter-m-phenylene-3-oxa-16-methyl-17-phenyl-4,5,6,18,19,20-hexanor-13,14-dihydro-;
3,7-Inter-m-phenylene-3-oxa-16,16-dimethyl-17-phenyl-4,5,6,18,19,20-hexanor-13,14-dihydro-;
3,7-Inter-m-phenylene-3-oxa-16-fluoro-17-phenyl-4,5,6,18,19,20-hexanor-13,14-dihydro-;
3,7-Inter-m-phenylene-3-oxa-16,16-difluoro-17-phenyl-4,5,6,18,19,20-hexanor-13,14-dihydro-;
3,7-Inter-m-phenylene-3-oxa-16-phenoxy-4,5,6,17,18,19,20-heptanor-13,14-dihydro-;
3,7-Inter-m-phenylene-3-oxa-16-(m-trifluoromethylphenoxy)-4,5,6,17,18,19,20-heptanor-13,14-dihydro-;
3,7-Inter-m-phenylene-3-oxa-16-(m-chlorophenoxy)-4,5,6,17,18,19,20-heptanor-13,14-dihydro-;
3,7-Inter-m-phenylene-3-oxa-16-(p-fluorophenoxy)-4,5,6,17,18,19,20-heptanor-13,14-dihydro-;
3,7-Inter-m-phenylene-3-oxa-16-phenoxy-4,5,6,18,19,20-hexanor-13,14-dihydro-;
3,7-Inter-m-phenylene-3-oxa-16-methyl-16-pehnoxy-4,5,6,18,19,20-hexanor-13,14-dihydro-;
3,17-Inter-m-phenylene-4,5,6-trinor-;
3,7-Inter-m-phenylene-4,5,6-trinor-16-methyl-;
3,7-Inter-m-phenylene-4,5,6-trinor-16,16-dimethyl-;
3,7-Inter-m-phenylene-4,5,6-trinor-16-fluoro-;
3,7-Inter-m-phenylene-4,5,6-trinor-16,16-difluoro-;
3,7-Inter-m-phenylene-17-phenyl-4,5,6,18,19,20-hexanor-;
3,7-Inter-m-phenylene-17-(m-trifluoromethylphenyl)-4,5,6,18,19,20-hexanor-;
3,7-Inter-m-phenylene-17-(m-chlorophenyl)-4,5,6,18,19,20-hexanor-;
3,7-Inter-m-phenylene-17-(p-fluorophenyl)-4,5,6,18,19,20-hexanor-;
3,7-Inter-m-phenylene-16-methyl-17-phenyl-4,5,6,18,19,20-hexanor-;
3,7-Inter-m-phenylene-16,16-dimethyl-17-phenyl-4,5,6,18,19,20-hexanor-;
3,7-Inter-m-phenylene-16-fluoro-17-phenyl-4,5,6,18,19,20-hexanor-;
3,7-Inter-m-phenylene-16,16-difluoro-17-phenyl-4,5,6,18,19,20-hexanor-;
3,7-Inter-m-phenylene-16-phenoxy-17-phenyl-4,5,6,17,18,19,20-heptanor-;
3,7-Inter-m-phenylene-16-(m-trifluoromethylphenoxy)-4,5,6,17,18,19,20-heptanor-;
3,7-Inter-m-phenylene-16-(m-chlorophenoxy)-4,5,6,17,18,19,20-heptanor-;
3,7-Inter-m-phenylene-16-(p-fluorophenoxy)-4,5,6,17,18,19,20-heptanor-;
3,7-Inter-m-phenylene-16-phenoxy-4,5,6,18,19,20-hexanor-;
3,7-Inter-m-phenylene-16-methyl-16-phenoxy-4,5,6,18,19,20-hexanor-;
3,7-Inter-m-phenylene-4,5,6-trinor-13,14-didehydro-;
3,7-Inter-m-phenylene-4,5,6-trinor-16-methyl-13,14-didehydro-;
3,7-Inter-m-phenylene-4,5,6-trinor-16,16-dimethyl-13,14-didehydro-;
3,7-Inter-m-phenylene-4,5,6-trinor-16-fluoro-13,14-didehydro-;
3,7-Inter-m-phenylene-4,5,6-trinor-16,16-difluoro-13,14-didehydro-;
3,7-Inter-m-phenylene-17-phenyl-4,5,6,18,19,20-hexanor-13,14-didehydro-;
3,7-Inter-m-phenylene-17-(m-trifluoromethylphenyl)-4,5,6,18,19,20-hexanor-13,14-didehydro-;
3,7-Inter-m-phenylene-17-(m-chlorophenyl)-4,5,6,18,19,20-hexanor-13,14-didehydro-;
3,7-Inter-m-phenylene-17-(p-fluorophenyl)-4,5,6,18,19,20-hexanor-13,14-didehydro-;
3,7-Inter-m-phenylene-16-methyl-17-phenyl-4,5,6,18,19,20-hexanor-13,14-didehydro-;
3,7-Inter-m-phenylene-16,16-dimethyl-17-phenyl-4,5,6,18,19,20-hexanor-13,14-didehydro-;
3,7-Inter-m-phenylene-16-fluoro-17-phenyl-4,5,6,18,19,20-hexanor-13,14-didehydro-;
3,7-Inter-m-phenylene-16,16-difuoro-17-phenyl-4,5,6,18,19,20-hexanor-13,14-didehydro-;
3,7-Inter-m-phenylene-16-phenoxy-4,5,6,17,18,19,20-heptanor-13,14-didehydro-;

3,7-Inter-m-phenylene-16-(m-trifluoromethylphenoxy)-4,5,6,17,18,19,20-heptanor-13,14-didehydro-;
3,7-Inter-m-phenylene-16-(m-chlorophenoxy)-4,5,6,17,18,19,20-heptanor-13,14-didehydro-;
3,7-Inter-m-phenylene-16-phenoxy-4,5,6,18,19,20-hexanor-13,14-didehydro-;
3,7-Inter-m-phenylene-16-methyl-16-phenoxy-4,5,6,18,19,20-hexanor-13,14-didehydro-;
3,7-Inter-m-phenylene-4,5,6-trinor-13,14-didehydro-;
3,7-Inter-m-phenylene-4,5,6-trinor-16-methyl-13,14-dihydro-;
3,7-Inter-m-phenylene-4,5,6-trinor-16,16-dimethyl-13,14-dihydro-;
3,7-Inter-m-phenylene-4,5,6-trinor-16-fluoro-13,14-dihydro-;
3,7-Inter-m-phenylene-4,5,6-trinor-16,16-difluoro-13,14-dihydro-;
3,7-Inter-m-phenylene-17-phenyl-4,5,6,18,19,20-hexanor-13,14-dihydro-;
3,7-Inter-m-phenylene-17-(m-trifluoromethylphenyl)-4,5,6,18,19,20-hexanor-13,14-dihydro-;
3,7-Inter-m-phenylene-17-(m-chlorophenyl)-4,5,6,18,19,20-hexanor-13,14-dihydro-;
3,7-Inter-m-phenylene-17-(p-fluorophenyl)-4,5,6,18,19,20-hexanor-13,14-dihydro-;
3,7-Inter-m-phenylene-16-methyl-17-phenyl-4,5,6,18,19,20-hexanor-13,14-dihydro-;
3,7-Inter-m-phenylene-16,16-dimethyl-17-phenyl-4,5,6,18,19,20-hexanor-13,14-dihydro-;
3,7-Inter-m-phenylene-16-fluoro-17-phenyl-4,5,6,18,19,20-hexanor-13,14-dihydro-;
3.7-Inter-m-phenylene-16,16-difluoro-17-phenyl-4,5,6,18,19,20-hexanor-13,14-dihydro-;
3,7-Inter-m-phenylene-16-phenoxy-4,5,6,17,18,19,20-heptanor-13,14-dihydro-;
3,7-Inter-m-phenylene-16-(m-trifluoromethylphenoxy)-4,5,6,17,18,19,20-heptanor-13,14-dihydro-;
3,7-Inter-m-phenylene-16-(m-chlorophenoxy)-4,5,6,17,18,19,20-heptanor-13,14-dihydro-;
3,7-Inter-m-phenylene-16-(p-fluorophenoxy)-4,5,6,17,18,19,20-heptanor-13,14-dihydro-;
3,7-Inter-m-phenylene-16-phenoxy-4,5,6,18,19,20-hexanor-13,14-dihydro-;
3,7-Inter-m-phenylene-16-methyl-16-phenoxy-4,5,6,18,19,20-hexanor-13,14-dihydro-;
4,4,5,5-Tetradehydro-;
4,4,5,5-Tetradehydro-16-methyl-;
4,4,5,5-Tetradehydro-16,16-dimethyl-;
4,4,5,5-Tetradehydro-16-fluoro-;
4,4,5,5-Tetradehydro-16,16-difluoro-;
4,4,5,5-Tetradehydro-17-phenyl-18,19,20-trinor-;
4,4,5,5-Tetradehydro-17-(m-trifluoromethylphenyl)-18, 19,20-trinor-;
4,4,5,5-Tetradehydro-17-(m-chlorophenyl)-18,19,20-trinor-;
4,4,5,5-Tetradehydro-17-(p-fluorophenyl)-18,19,20-trinor-;
4,4,5,5-Tetradehydro-16-methyl-17-phenyl-18,19,20-trinor-;
4,4,5,5-Tetradehydro-16,16-Dimethyl-17-phenyl-18,19,20-trinor-;
4,4,5,5-Tetradehydro-16-fluoro-16-phenyl-18,19,20-trinor-;
4,4,5,5-Tetradehydro-16,16-difluoro-17-phenyl-18,19,20-trinor-;
4,4,5,5-Tetradehydro-16-phenoxy-17,18,19,20-tetranor-;
4,4,5,5-Tetradehydro-16-(m-trifluoromethylphenoxy)-17,18,19,20-tetranor-;
4,4,5,5-Tetradehydro-16-(m-chlorophenoxy)-17,18,19,20-tetranor-;
4,4,5,5-Tetradehydro-16-(p-fluorphenoxy)-17,18,19,20-tetranor-;
4,4,5,5-Tetradehydro-16-phenoxy-18,19,20-trinor-;
4,4,5,5-Tetradehydro-16-methyl-16-phenoxy-18,19,20-trinor-;
4,4,5,5,13,14-Hexadehydro-;
4,4,5,5,13,14-Hexadehydro-16-methyl-;
4,4,5,5,13,14-Hexadehydro-16,16-dimethyl-;
4,4,5,5,13,14-Hexadehydro-16-fluoro-;
4,4,5,5,13,14-Hexadehydro-16,16-difluoro-;
4,4,5,5,13,14-Hexahydro-17-phenyl-18,19,20-trinor-;
4,4,5,5,13,14-Hexadehydro-17-(m-trifluoromethylphenyl)-18,19,20-trinor-;
4,4,5,5,13,14-Hexadehydro-17-(m-chlorophenyl)-18,19,20-trinor-;
4,4,5,5,13,14-Hexadehydro17-(p-fluorophenyl)-18,19,20-trinor-;
4,4,5,5,13,14-Hexadehydro-16-methyl-17-phenyl-18,19,20-trinor-;
4,4,5,13,14-Hexadehydro-16,16-dimethyl-17-phenyl-18,19,20-trinor-13,14-didehydro-;
4,4,5,5,13,14-Hexadehydro-16-fluoro-17-phenyl-18,19,20-trinor-;
4,4,5,5,13,14-Hexadehydro-16,16-difluoro-17-phenyl-18,19,20-trinor-;
4,4,5,5,13,14-Hexadehydro-16-phenoxy-17,18,19,20-tetranor-;
4,4,5,5,13,14-Hexadehydro-16-(m-trifluoromethylphenoxy)-17,18,19,20-tetranor;
4,4,5,5,13,14-Hexadehydro-16-(m-chlorophenoxy)-17,18,19,20-tetranor-;
4,4,5,5,13,14-Hexadehydro-16-methyl-16-phenoxy-18,19,20-trinor-;
4,4,5,5-Tetradehydro-13,14-dihydro-;
4,4,5,5-Tetradehydro-16-methyl-13,14-dihydro-;
4,4,5,5-Tetradehydro-16,16-dimethyl-13,14-dihydro-;
4,4,5,5-Tetradehydro-16-fluoro-13,14-dihydro-;
4,4,5,5-Tetradehydro-16,16-difluoro-13,14-dihydro-;
4,4,5,5,-Tetradehydro-16,16-difluoro-13,14-dihydro-;
4,4,5,5-Tetradehydro-17-phenyl-18,19,20-trinor-13,14-dihydro-;
4,4,5,5-Tetradehydro-17-(m-trifluoromethylphenyl)-18,19,20-trinor-13,14-dihydro-;
4,4,5,5-Tetradehydro-17-(m-chlorophenyl)-18,19,20-trinor-13,14-dihydro-;
4,4,5,5-Tetradehydro-17-(p-fluorophenyl)-18,19,20-trinor-13,14-dihydro-;
4,4,5,5-Tetradehydro-16-methyl-17-phenyl-18,19,20-trinor-13,14-dihydro-;
4,4,5,5-Tetradehydro-16,16-Dimethyl-17-phenyl-18,19,20-trinor-13,14-dihydro-;
4,4,5,5-Tetradehydro-16-fluoro-17-phenyl-18,19,20-trinor-13,14-dihydro-;
4,4,5,5-Tetradehydro-16,16-difluoro-17-phenyl-18,19,20-trinor-13,14-dihydro-;
4,4,5,5-Tetradehydro-16-phenoxy-17,18,19,20-tetranor-13,14-dihydro-;

4,4,5,5-Tetradehydro-16-(m-trifluoromethylphenoxy)-17,18,19,20-tetranor-13,14-dihydro-;
4,4,5,5-Tetradehydro-16-(m-chlorophenoxy)-17,18,19,20-tetranor-13,14-dihydro-;
4,4,5,5-Tetradehydro-16-(p-fluorophenoxy)-17,18,19,20-tetranor-13,14-dihydro-;
4,4,5,5-Tetradehydro-16-phenoxy-18,19,20-trinor-13,14-dihydro-;
4,4,5,5-Tetradehydro-16-methyl-16-phenoxy-18,19,20-trinor-13,14-dihydro-.
5-Oxa-;
5-Oxa-16-methyl-;
5-Oxa-16,16-dimethyl-;
5-Oxa-16-fluoro-;
5-Oxa-16,16-difluoro-;
5-Oxa-17-phenyl-18,19,20-trinor-;
5-Oxa-17-(m-trifluoromethylphenyl)-18,19,20-trinor-;
5-Oxa-17-(m-chlorophenyl)-18,19,20-trinor-;
5-Oxa-17-(p-fluorophenyl)-18,19,20-trinor-;
5-Oxa-16-methyl-17-phenyl-18,19,20-trinor-;
5-Oxa-16,16-dimethyl-17-phenyl-18,19,20-trinor-;
5-Oxa-16-fluoro-17-phenyl-18,19,20-trinor-;
5-Oxa-16,16-difluoro-17-phenyl-18,19,20-trinor-;
5-Oxa-16-phenoxy-17,18,19,20-tetranor-;
5-Oxa-16-(m-trifluoromethylphenoxy)-17,18,19,20-tetranor-;
5-Oxa-16-(m-chlorophenoxy)-17,18,19,20-tetranor-;
5-Oxa-16-(p-fluorophenoxy)-17,18,19,20-tetranor-;
5-Oxa-16-phenoxy-18,19,20-trinor-;
5-Oxa-16-methyl-16-phenoxy-18,19,20-trinor-;
5-Oxa-16-methyl-13,14-didehydro-;
5-Oxa-16,16-dimethyl-13,14-didehydro-;
5-Oxa-16-fluoro-13,14-didehydro-;
5-Oxa-16,16-difluoro-13,14-didehydro-;
5-Oxa-17-phenyl-18,19,20-trinor-13,14-didehydro-;
5-Oxa-17-(m-trifluoromethylphenyl)-18,19,20-trinor-13,14-didehydro-;
5-Oxa-17-(m-chlorophenyl)-18,19,20-trinor-13,14-didehydro-;
5-Oxa-17-(p-fluorophenyl)-18,19,20-trinor-13,14-didehydro-;
5-Oxa-16-methyl-17-phenyl-18,19,20-trinor-13,14-didehydro-;
5-Oxa-16,16-dimethyl-17-phenyl-18,19,20-trinor-13,14-didehydro-;
5-Oxa-16-fluoro-17-phenyl-18,19,20-trinor-13,14-didehydro-;
5-Oxa-16,16-difluoro-17-phenyl-18,19,20-trinor-13,14-didehydro-;
5-Oxa-16-phenoxy-17,18,19,20-tetranor-13,14-didehydro-;
5-Oxa-16-(m-trifluoromethylphenoxy)-17,18,19,20-tetranor-13,14-didehydro-;
5-Oxa-16-(m-chlorophenoxy)-17,18,19,20-tetranor-13,14-didehydro-;
5-Oxa-16-phenoxy-18,19,20-trinor-13,14-didehydro-;
5-Oxa-16-methyl-16-phenoxy-18,19,20-trinor-13,14-didehydro-;
5-Oxa-13,14-dihydro-;
5-Oxa-16-methyl-13,14-dihydro-; ;
5-Oxa-16,16-dimethyl-13,14-dihydro-;
5-Oxa-16-fluoro-13,14-dihydro-;
5-Oxa-16,16-difluoro-13,14-dihydro-;
5-Oxa-17-phenyl-18,19,20-trinor-13,14-dihydro-;
5-Oxa-17-(m-trifluoromethylphenyl)-18,19,20-trinor-13,14-dihydro-;
5-Oxa-17-(m-chlorophenyl)-18,19,20-trinor-13,14-dihydro-;
5-Oxa-17-(p-fluorophenyl)-18,19,20-trinor-13,14-dihydro-
5-Oxa-16-methyl-17-phenyl-18,19,20-trinor-13,14-dihydro-;
5-Oxa-16,16-Dimethyl-17-phenyl-18,19,20-trinor-13,14-dihydro-;
5-Oxa-16-fluoro-17-phenyl-18,19,20-trinor-13,14-dihydro-;
5-Oxa-16,16-difluoro-17-phenyl-18,19,20-trinor-13,14-dihydro-;
5-Oxa-16-phenoxy-17,18,19,20-tetranor-13,14-dihydro-;
5-Oxa-16-(m-trifluoromethylphenoxy)-17,18,19,20-tetranor-13,14-dihydro-;
5-Oxa-16-(m-chlorophenoxy)-17,18,19,20-tetranor-13,14-dihydro-;
5-Oxa-16-(p-fluorophenoxy)-17,18,19,20-tetranor-13,14-dihydro-;
5-Oxa-16-phenoxy-18,19,20-trinor-13,14-dihydro-;
5-Oxa-16-methyl-16-phenoxy-18,19,20-trinor-13,14-dihydro-;

Following the procedure of Example 1, but employing corresponding starting material as described above there are prepared 9,11,15-trideoxy-9α,11α-epoxymethano- or 11α, 9α-epoxymethano-PGF$_2$-type compounds, in free acid or methyl ester form, which exhibit the following functional characteristics:
5,6-Didehydro-;
5,6-Didehydro-16-methyl-;
5,6-Didehydro-16,16-dimethyl-;
5,6-Didehydro-16-fluoro-;
5,6-Didehydro-16,16-difluoro-;
5,6-Didehydro-17-phenyl-18,19,20-trinor-;
5,6-Didehydro-17-(m-trifluoromethylphenyl)-18,19,20-trinor-;
5,6-Didehydro-17-(m-chlorophenyl)-18,19,20-trinor-;
5,6-Didehydro-17-(p-fluorophenyl)-18,19,20-trinor-;
5,6-Didehydro-16-methyl-17-phenyl-18,19,20-trinor-;
5,6-Didehydro-16,16-Dimethyl-17-phenyl-18,19,20-trinor-;
5,6-Didehydro-16-fluoro-17-phenyl-18,19,20-trinor-;
5,6-Didehydro-16,16-difluoro-17-phenyl-18,19,20-trinor-;
5,6-Didehydro-16-phenoxy-17,18,19,20-tetranor-;
5,6-Didehydro-16-(m-trifluoromethylphenoxy)-17,18,19,20-tetranor-;
5,6,-Didehydro-16-(m-chlorophenoxy)-17,18,19,20-tetranor;
5,6-Didehydro-16-(p-fluorophenoxy)-17,18,19,20-tetranor-;
5,6-Didehydro-16-phenoxy-18,19,20-trinor-;
5,6-Didehydro-16-methyl-16-phenoxy-18,19,20-trinor-;
5,6,13,14-Tetradehydro-;
5,6,13,14-Tetradehydro-16-methyl-;
5,6,13,14-Tetradehydro-16,16-dimethyl-;
5,6,13,14-Tetradehydro-16-fluoro-;
5,6,13,14-Tetradehydro-16,16-difluoro-;
5,6,13,14-Tetradehydro-17-phenyl-18,19,20-trinor-;

5,6,13,14-Tetradehydro-17-(m-trifluoromethylphenyl)-18,19,20-trinor-;

5,6,13,14-Tetradehydro-17-(m-chlorophenyl)-18,19,20-trinor-;

5,6,13,14-Tetradehydro-17-(p-fluorophenyl)-18,19,20-trinor-;

5,6,13,14-Tetradehydro-16-methyl-17-phenyl-18,19,20-trinor-;

5,6,13,14-Tetradehydro-16,16-dimethyl-17-phenyl-18,19,20-trinor-;

5,6,13,14-Tetradehydro-16-fluoro-17-phenyl-18,19,20-trinor-;

5,6,13,14-Tetradehydro-16,16-difluoro-17-phenyl-18,19,20-trinor-;

5,6,13,14-Tetradehydro-16-phenoxy-17,18,19,20-tetranor-;

5,6,13,14-Tetradehydro-16-(m-trifluoromethylphenoxy)-17,18,19,20-tetranor-;

5,6,13,14-Tetradehydro-16-(m-chlorophenoxy)-17,18,19,20-tetranor-;

5,6,13,14-Tetradehydro-16-phenoxy-18,19,20-trinor-;

5,6,13,14-Tetradehydro-16-methyl-16-phenoxy 18,19,20-trinor-;

5,6-Didehydro-16-methyl-3,14-dihydro-;

5,6-Didehydro-16,16-dimethyl-13,14-dihydro-;

5,6-Didehydro-16-fluoro-13,14-dihydro-;

5,6-Didehydro-16,16-difluoro-13,14-dihydro-;

5,6-Didehydro-17-phenyl-18,19,20-trinor-13,14-dihydro-;

5,6-Didehydro-17-(m-trifluoromethylphenyl)-18,19,20trinor-13,14-dihydro-;

5,6-Didehydro-17-(m-chlorophenyl)-18,19,20-trinor-13,14-dihydro-;

5,6-Didehydro-17-(p-fluorophenyl)-18,19,20-trinor-13,14-dihydro-;

5,6-Didehydro-16-methyl-17-phenyl-18,19,20-trinor-13,14-dihydro-;

5,6-Didehydro-16,16-dimethyl-17-phenyl-18,19,20trinor-13,14-dihydro-;

5,6-Didehydro-16-fluoro-17-phenyl-18,19,20-trinor-;

5,6-Didehydro-16,16-Difluoro-17-phenyl-18,19,20-trinor-13,14-dihydro-;

5,6-Didehydro-16-phenoxy-17,18,19,20-tetranor-13,14-dihydro-;

5,6-Didehydro-16-(m-trifluoromethylphenoxy)-17,18,19,20-tetranor-13,14-dihydro-;

5,6-Didehydro-16-(m-chlorophenoxy)-17,18,19,20-tetranor-13,14-dihydro-;

5,6-Didehydro-16-(p-fluorophenoxy)-17,18,19,20-tetranor-13,14-dihydro-;

5,6-Didehydro-16-phenoxy-18,19,20-trinor-13,14-dihydro-;

5,6-Didehydro-16-methyl-16-phenoxy-18,19,20-trinor-13,14-dihydro-,

EXAMPLE 7

2-Decarboxy-2-hydroxymethyl-9,11,15-trideoxy-9α,11α-epoxymethano-PGF$_1$ (Formula XCII: $Z_1$ is cis-CH=CH-(CH$_2$)$_3$-, $L_4$ is oxa, $L_5$ is a valence bond, $Y_1$ is trans-CH=CH-, $R_3$ and $R_4$ of the $L_1$ moiety are both hydrogen, and $R_7$ is n-butyl).

Refer to Chart F.

750 mg. of 9,11,15-trideoxy-9α,11α-epoxymethano-PGF$_1$, methyl ester, dissolved in 50 ml. of diethyl ether are reacted with 500 mg. of lithium aluminum hydride at room temperature, with stirring. When the starting material is completely consumed (as indicated by thin layer chromatographic analysis) one ml. of water is cautiously added. Thereafter 0.8 ml. of 10 percent aqueous sodium hydroxide is added and the resulting mixture allowed to stir for 12 hr. Thereupon magnesium sulfate is added with stirring and the stirred mixture then filtered through magnesium sulfate and evaporated to a residue, which contains pure title product.

Following the procedure of Example 7, but employing each of the various formula XCI 9,11,15-trideoxy-9α, 11α-or 11α,9α-epoxymethano-PGF-type compounds, there are prepared each of the various corresponding 2-decarboxy-2-hydroxymethyl-9,11,15-trideoxy-9α, 11α- or 11α, 9α-epoxymethano-PGF-type products.

EXAMPLE 8

2-Decarboxy-2-aminomethyl-9,11,15-trideoxy- 9α,1-1α-epoxymethano-PGF$_1$ (Formula CIV: $Z_1$, $L_4$, $L_5$, $Y_1$, $L_1$, and $R_7$ are as defined in Example 7).

Refer to Chart G.

A. 9,11,15-Trideoxy-9α,11α-epoxymethano-PGF$_1$, methyl ester is dissolved in one ml. of 95 percent ethanol. The resulting mixture is then transferred to a steel Parr bomb rinsed with 2 one-half ml. aliquots of 95 percent ethanol and 200 mg. of ammonium chloride are added. Then the mixture is cooled in a dry ice acetone bath and ammonia is added until about 5 to 10 ml. has condensed. The bomb is then sealed and allowed to warm to room temperature. Thereafter the bomb is placed in an oven at 50° C. for 2 days cooled in a dry-ice acetone bath, and opened. Thereafter residual ammonia is evaporated with nitrogen and the product extracted with ethyl acetate, washed with water and saturated brine, dried over sodium sulfate, and evaporated to yield 9,11,15-trideoxy-9α,11α-epoxymethano-PGF$_1$ amide, formula CIII B. Lithium aluminum hydride (100 mg.) in 5 ml. of dry tetrahydrofuran under nitrogen is prepared. A solution of the reaction product of part A is then slowly added (being dissolved in a small amount of dry tetrahydrofuran). The resulting mixture is then stirred at room temperature for 48 hr. and thereafter one-tenth ml. of water is added while cooling the mixture in an ice bath. Thereafter 0.1 ml. of 15 percent sodium hydroxide and 0.3 ml. of water is added. The suspension is then filtered; dried over magnesium sulfate; washed with ethyl acetate; and evaporated to yield a residue of the title product.

Following the procedure of Example 8, but employing each of the various formula Cl 9,11,15-trideoxy-9α,11α- or 11α,9α-epoxymethanol-PGF-type compounds, there are prepared each of the various corresponding 2-decarboxy-2-aminomethyl-9,11,15-trideoxy-9α,11α-or 11α,9α-epoxymethano-PGF-type products.

I claim:

1. A process for preparing a prostaglandin analog of the formula:

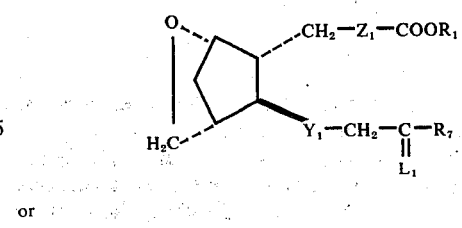

or

-continued

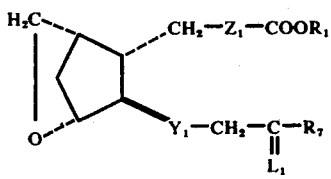

wherein $Y_1$ is trans—CH=CH—, —C≡C—, or —CH$_2$CH$_2$—; wherein $L_1$ is

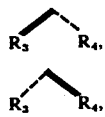

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro; wherein $Z_1$ is
1. cis—CH=CH—CH$_2$—(CH$_2$)$_g$—CH$_2$—,
2. cis—CH=CH—CH$_2$—(CH$_2$)$_g$—CF$_2$—,
3. cis-CH$_2$-CH=CH-(CH$_2$)$_g$—CH$_2$—,
4. —(CH$_2$)$_3$—(CH$_2$)$_g$—CH$_2$—,
5. —(CH$_2$)$_3$—(CH$_2$)$_g$—CF$_2$—,
6. —CH$_2$—O—CH$_2$—(CH$_2$)$_g$—CH$_2$—,
7. —C≡C-CH$_2$-(CH$_2$)$_g$—CH$_2$—,
8. —CH$_2$—O≡C-(CH$_2$)$_g$—CH$_2$—,

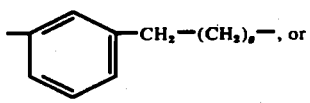 (9)

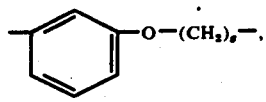 (10)

wherein $g$ is one, 2, or 3;
wherein $R_7$ is
1. —(CH$_2$)$_m$—CH$_3$,

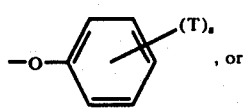 (2)

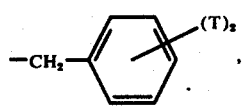 (3)

wherein $l$ is zero to three, inclusive, wherein $m$ is one to 5, inclusive, T is chloro, fluoro, trifluoromethyl, alkyl of one to 3 carbon atoms, inclusive, or alkoxy of one to 3 carbon atoms, inclusive, and $s$ is zero, one, 2, or 3, the various T's being the same or different, with the proviso that not more than two T's are other than alkyl, with the further proviso that $R_7$ is

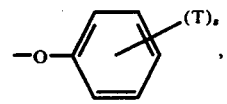

wherein T and $s$ are as defeind above, only when $R_3$ and $R_4$ are hydrogen or methyl, being the same or different; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, with the proviso that $Z_1$ is —(CH$_2$)$_3$—(CH$_2$)$_g$—CH$_2$—, $Y_1$ is —CH$_2$CH$_2$—, and $R_3$ and $R_4$ are both hydrogen, only when $R_7$ is not —(CH$_2$)$_m$—CH$_3$; which comprises:
1. sulfonating the ring hydroxyl of prostaglandin-type compound of the formula

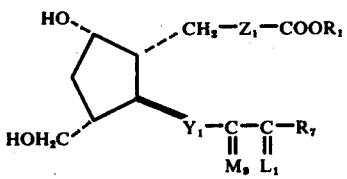

or

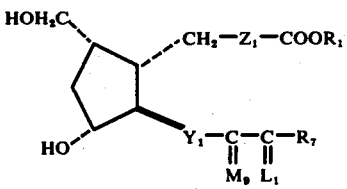

respectively, wherein $M_9$ is

or

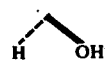

and wherein $L_1$, $R_1$, $R_7$, $R_8$, $Y_1$, and $Z_1$ are as defined above;
2. cyclizing the reaction product of step 1;
3. deoxygenating the secondary hydroxyl of the reaction product of step 2.

2. A process for preparing a prostaglandin analog of the formula

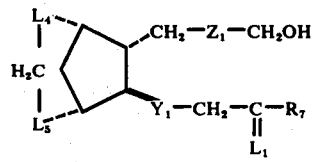

wherein $Y_1$ is trans—CH=CH—, —O=C—, or —CH$_2$CH$_2$—;
wherein one of $L_4$ and $L_5$ is oxa and the other is a valence bond;
wherein $L_1$ is

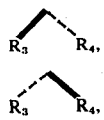

or a mixture of

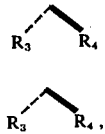

and wherein $R_3$ and $R_4$ are hydrogen, methyl, or fluoro, being the same or different, with the proviso that one of $R_3$ and $R_4$ is fluoro only when the other is hydrogen or fluoro; wherein $Z_1$ is
1. cis-CH=CH—CH$_2$—(CH$_2$)$_g$—CH$_2$—,
2. cis—CH=CH—CH$_2$—(CH$_2$)$_g$—CF$_2$ —,
3. cis—CH$_2$-CH=CH—(CH$_2$)$_g$—CH$_2$—,
4. —(CH$_2$)$_3$—(CH$_2$)$_g$—CH$_2$—,
5. —(CH$_2$)$_3$—(CH$_2$)$_g$—CF$_2$—,
6. —CH$_2$—O—CH$_2$—(CH$_2$)$_g$—CH$_2$—,
7. –O=C-CH$_2$-(CH$_2$)$_g$-CH$_2$-,
8. —CH$_2$-O=C—(CH$_2$)$_g$—CH$_2$—,

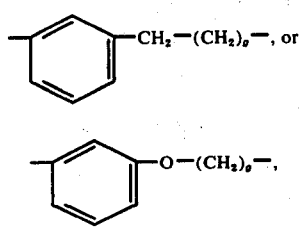 (9)

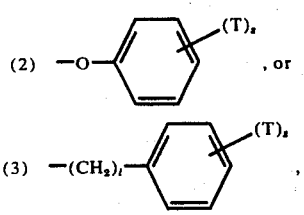 (10)

wherein g is one, 2, or 3;
wherein $R_7$ is
1. —(CH$_2$)$_m$—CH$_3$, (2) 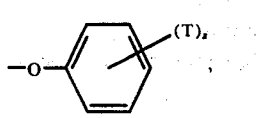, or (3) —(CH$_2$)$_l$—[phenyl ring with (T)$_s$], wherein l is zero to 3, inclusive, wherein m is one to 5, inclusive, T is chloro, fluoro,
trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is wherein T and s are as defined above, only when $R_3$ and $R_4$ are hydrogen or methyl, being the same or different; and which comprises:
1. reducing a prostaglandin analog of the formula:

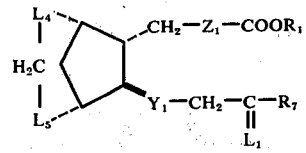

wherein $L_1$, $L_4$, $L_5$, $R_7$, $R_8$, $Y_1$, and $Z_1$ are as defined above, and
wherein $R_1$ is hydrogen or an ester; to a corresponding primary alcohol.
3. A process for preparing a prostaglandin analog of the formula

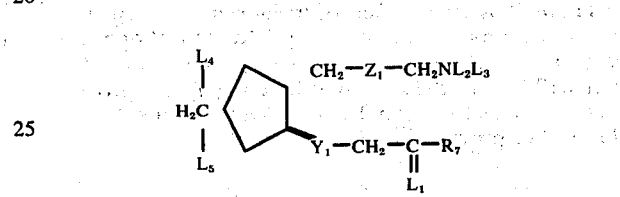

wherein $Y_1$ is trans—CH=CH—, —O=C—, or —CH$_2$CH$_2$—;
wherein one of $L_4$ and $L_5$ is oxa and the other is a valence bond;
wherein $L_1$ is

or a mixture of

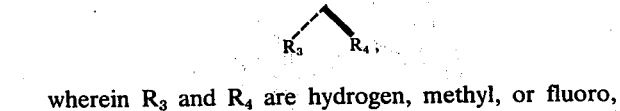

and wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
1. cis—CH=CH-CH$_2$—(CH$_2$)$_g$-CH$_2$—,
2. cis—CH=Ch—Ch$_2$—(CH$_2$)$_g$-CF$_2$—,
2. cis—CH$_2$—CH=CH-(CH$_2$)$_g$—CH$_2$—,
4. —(CH$_2$)$_3$—(CH$_2$)$_g$-CH$_2$—,
5. —(CH$_2$)$_3$—(CH$_2$)$_g$—CF$_2$—,
6. —CH$_2$—CH—(CH$_2$—(CH$_2$)$_g$—CH$_2$—,
7. -C C-CH$_2$—(CH$_2$)$_g$—(CH$_2$—,
8. (—CH$_2$—C C-(CH$_2$)$_g$-(CH$_2$—,

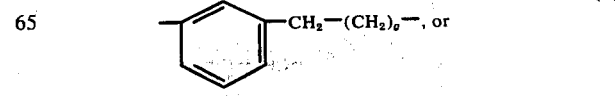 (9)

-continued

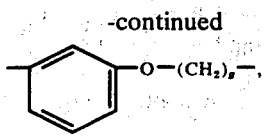
(10)

wherein g is one, 2, or 3;
wherein $R_7$ is
1. $-(CH_2)_m-CH_3$,

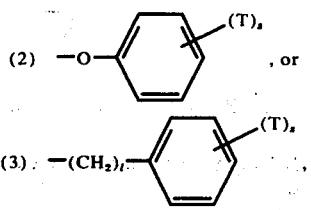
(2), or (3)

wherein $l$ is zero to 3, inclusive, wherein $m$ is one to 5, inclusive, T is chloro, fluoro, trifluoromethyl, alkyl of one to 3 carbon atoms, inclusive, or alkoxy of one to 3 carbon atoms, inclusive, and $s$ is zero, one, 2, or 3, the various T's being the same or different, with the proviso that not more than two T's are other than alkyl, with the further proviso that $R_7$ is

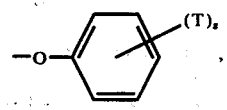

wherein T and $s$ are as defined above, only when $R_3$ and $R_4$ are hydrogen or methyl, being the same or different; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
which comprises;
aminating a prostaglandin analog of the formula

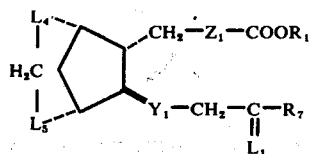

wherein $L_1$, L, $L_5$, $R_1$, $R_7$, $R_8$, $Y_1$, and $Z_1$ are as defined above.

4. A prostaglandin analog of the formula

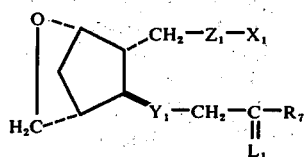
or
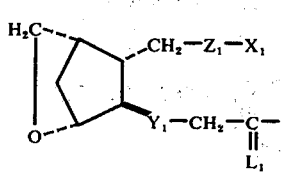

wherein $Y_1$ is trans—CH=CH—, -C ≡ C-, or —$CH_2CH_2$—; wherein $L_1$ is

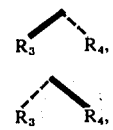

or a mixture of

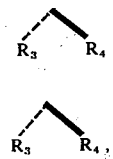

and

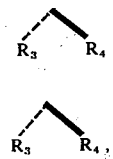

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
1. cis-CH=CH—$CH_2$—$(CH_2)_g$—$CH_2$—,
2. cis-CH=CH—$CH_2$—$(CH_2)_g$—$CF_2$—,
3. cis-$CH_2$—CH=CH—$(CH_2)_g$—$CH_2$—,
4. —$(CH_2)_3$—$(CH_2)_g$—$CH_2$—,
5. —$(CH_2)_3$—$(CH_2)_g$—$CF_2$—,
6. —$CH_2$—O—$CH_2$—$(CH_2)_g$—$CH_2$—,
7. —O ≡ C—$CH_2$—$(CH_2)_g$—$CH_2$—,
8. —$CH_2$—O ≡ C—$(CH_2)_g$—$CH_2$—,

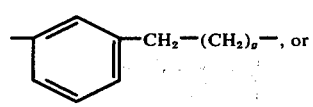
(9)

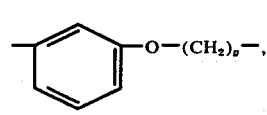
(10)

wherein g is one, 2, or 3;
wherein $R_7$ is
1. —$(CH_2)_m$—$CH_3$,

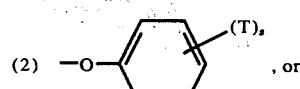
(2), or

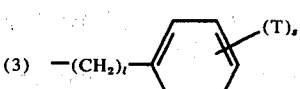
(3)

wherein $l$ is zero to 3, inclusive, wherein $m$ is one to 5, inclusive, T is chloro, fluoro, trifluoromethyl, akyl of one to 3 carbon atoms, inclusive, or alkoxy of one to 3 carbon atoms, inclusive, and $s$ is zero, one, 2, or 3, the various T's being the same or different, with the proviso that not more than two T's are other than alkyl, with the further proviso that $R_7$ is

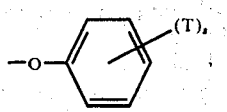

wherein T and s are as defined above, only when $R_3$ and $R_4$ are hydrogen or methyl, being the same or different; and wherein $X_1$ is

1. $-COOR_1$;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, 2. $-CH_2OH$, or

3. $-CH_2NL_2L_3$:

wherein $L_2$ and $L_3$ are hydrogen, or alkyl of one to 4 carbon atoms, inclusive;

with the proviso that $Z_1$ is $-(CH_2)_3-(CH_2)_g-$, $CH_2-$, $Y_1$ is $-CH_2CH_2-$, $R_3$ and $R_4$ are both hydrogen, and $R_7$ is $-(CH_2)_3-CH_3$, only when $X_1$ is not $COOR_1$.

5. A prostaglandin analog according to claim 4, wherein $X_1$ is $-CH_2OH$.

6. 2-Decarboxy-2-hydroxymethyl-9,11,15-trideoxy-9α,11α-epoxymethano-PGF$_2$, a prostaglandin analog according to claim 5.

7. A prostaglandin analog according to claim 4, wherein $X_1$ is $-CH_2NL_2L_3$.

8. 2-Decarboxy-2-aminomethyl-9,11,15-trideoxy-9α,11α-epoxymethano-PGF$_2$, a prostaglandin analog according to claim 7.

9. A prostaglandin analog according to claim 4, wherein $X_1$ is $-COOr_1$.

10. 9,11,15-Trideoxy-11α,9α-epoxymethano-PGF-type compounds according to claim 9.

11. 9,11,15-Trideoxy-11α,9α-epoxymethano-PGF$_2$, a prostaglandin analog according to claim 10.

12. 9,11,15-Trideoxy-11α,9α-epoxymethao-PGF$_1$, a prostaglandin analog according to claim 10.

13. 9,11,15-Trideoxy-9α,11α-epoxymethano-PGF-type compounds according to claim 9.

14. A prostaglandin analog according to claim 13, wherein $Y_1$ is $-C≡C-$.

15. 9,11,15-Trideoxy-9α,11α-epoxymethano-13,14-dihydro-PGF$_2$, a prostaglandin analog according to claim 14.

16. 9,11,15-Trideoxy-9α,11α-epoxymethano-13,14-didehydro-PGF, a prostaglandin analog according to claim 14.

17. A prostaglandin analog according to claim 13, wherein $Y_1$ is $-CH_2CH_2-$.

18. 9,11,15-Trideoxy-9α,11α-epoxymethano-PGF$_2$, a prostaglandin analog according to claim 17.

19. 9,11,15-Trideoxy-9α,11α-epoxymethano-PGF$_2$, methyl ester, a prostaglandin analog according to claim 17.

20. A prostaglandin analog according to claim 13, wherein $Y_1$ is trans—CH=CH.

21. A prostaglandin analog according to claim 20, wherein $Z_1$ is cis—CH=CH—$CH_2$—$(CH_2)_g$—$CF_2$—.

22. 9,11,15-Trideoxy-9α,11α-epoxymethano-2,2-difluoro PGF$_2$, a prostaglandin analog according to claim 21.

23. A prostaglandin analog according to claim 20, wherein $Z_1$ is cis—$CH_2$—CH=CH—$(CH_2)_g$—$CH_2$—.

24. 9,11,15-Trideoxy-9α,11α-epoxymethano-cis-4,5-didehydro-PGF$_2$, a prostaglandin analog according to claim 23.

25. A prostaglandin analog according to claim 20, wherein $Z_1$ is $-(CH_2)_3-(CH_2)_g-(CH_2-$.

26. 9,11,15-Trideoxy-9α,11α-epoxymethano-PGF$_1$, a prostaglandin analog according to claim 25.

27. A prostaglandin analog according to claim 20, wherein $Z_1$ is $-(CH_2)_3-(CH_2)_g-CD_2-$.

28. 9,11,15-Trideoxy-9α,11α-epoxymethao-2,2-difluoro-PGF$_1$, a prostaglandin analog according to claim 27.

29. A prostaglandin analog according to claim 20, wherein $Z_1$ is $-CH_2-O-CH_2-(CH_2)_g-CH_2-$.

30. 9,11,15-Trideoxy-9α,11α-epoxymethano-5-oxa-PGF$_1$, a prostaglandin analog according to claim 29.

31. A prostaglandin analog according to claim 20, wherein $Z_1$ is $-C≡C-CH_2-(CH_2)_g-CH_2-$.

32. 9,11,15-Trideoxy-9α,11α-epoxymethao-5,6-didehydro-PGF$_2$, a prostaglandin analog according to claim 31.

33. A prostaglandin analog according to claim 20, wherein $Z_1$ is $-CH_2-C≡C-(CH_2)_g-(CH_2-$.

34. 9,11,15-Trideoxy-9α,11α-epoxymethano-4,4,5,5-tetradehydro-PGF$_1$, a prostaglandin analog according to claim 33.

35. A prostaglandin analog according to claim 20, wherein $Z_1$ is

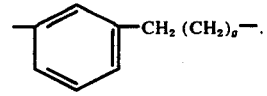

36. 9,11,15-Trideoxy-9α,11α-epoxymethano-3,7-inter-m-phenylene-4,5,6-trinor-PGF$_1$, a prostaglandin analog according to claim 35.

37. A prostaglandin according to claim 20, wherein $Z_1$ is

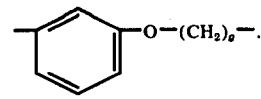

38. 9,11,15-Trideoxy-9α,11α-epoxymethano-3,7-inter-m-phenylene-3-oxa-4,5,6-trinor-PGF$_1$, a prostaglandin analog according to claim 37.

39. A prostaglandin analog according to claim 20, wherein $Z_1$ is cis–CH=CH—$CH_2$—$(CH_2)_g$—$CH_2$—.

40. A prostaglandin analog according to claim 39, wherein $R_7$

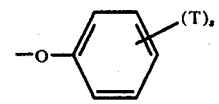

41. 9,11,15-Trideoxy-9α,11α-epoxymethano-16-phenoxy-17,18,19,20-tetrano-PGF$_2$, a prostaglandin analog according to claim 40.

42. A prostaglandin analog according to claim 39, wherein $R_7$ is

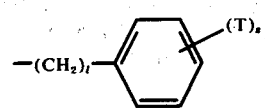

43. 9,11,15-Trideoxy-9α,11α-epoxymethao-17-phenyl-18,19,20-trinor-PGF$_2$, a prostaglandin analog according to claim 42.

44. A prostaglandin analog according to claim 39, wherein R$_7$ is —(CH$_2$)$_m$—CH$_3$.

45. A prostaglandin analog according to claim 44, wherein g is 3.

46. 9,11,15-Trideoxy-9α,11α-epoxymethano-2a,2b-dihomo-PGF$_2$, a prostaglandin analog according to claim 45.

47. A prostaglandin analog according to claim 44, wherein g is one.

48. A prostaglandin analog according to claim 47, wherein at least one of R$_3$ and R$_4$ is methyl.

49. A prostaglandin analog according to claim 48, wherein R$_3$ and R$_4$ are both methyl.

50. 9,11,15-Trideoxy-9α,11α-epoxymethano-16,16-dimethyl-PGF$_2$, methyl ester, a prostaglandin analog according to claim 49.

51. 9,11,15-Trideoxy-9α,11α-epoxymethano-16,16-dimethyl-PGF$_2$, a prostaglandin analog according to claim 49.

52. A prostaglandin analog according to claim 47, wherein at least one of R$_3$ and R$_4$ is fluoro.

53. A prostaglandin analog according to claim 52, wherein R$_3$ and R$_4$ are both fluoro.

54. 9,11,15-Trideoxy-9α,11α-epoxymethano-16,16-difluoro-PGF$_2$, methyl ester, a prostaglandin analog according to claim 53.

55. 9,11,15-Trideoxy-9α,11α-epoxymethano-16,16-difluoro-PGF$_2$, a prostaglandin analog according to claim 53.

56. A prostaglandin analog according to claim 47, wherein R$_3$ and R$_4$ are both hydrogen.

57. 9,11,15-Trideoxy-9α,11α-epoxymethano-PGF$_2$, methyl ester, a prostaglandin analog according to claim 56.

58. 9,11,15-Trideoxy-9α,11α-epoxymethano-PGF$_2$, a prostaglandin analog according to claim 56.

* * * * *

UNITED STATES PATENT OFFICE
CERTIFICATE OF CORRECTION

Patent No. 4,028,350  Dated 7 June 1977

Inventor(s) Gordon L. Bundy

It is certified that error appears in the above-identified patent and that said Letters Patent are hereby corrected as shown below:

In the Title, "9α,11αOR 11α9αEPOXYMETHANO-PROSTAGLANDANS" should read -- 9α,11α- or 11α9α-EPOXYMETHANO-PROSTAGLANDINS --;

Column 1, line 47, "11α,9αepoxymethano-prostane:-derviatives" should read -- 11α,9α-epoxymethano-prostane-derivatives --;

Column 2, line 17, "ctied above" should read -- cited above --; line 43, "preparation" should read -- preparing --;

Column 4, lines 61-62, "cis-CH=λCH-CH$_2$(CH$_2$)g-CF$_2$-" should read -- cis-CH=CH-CH$_2$-(CH$_2$)g-CF$_2$- --;

Column 5, line 2, "a though" should read -- as though --;

Column 9, line 34, "it is preferred that me be 3" should read -- it is preferred that m be 3 --;

Columns 15-16, the last formula,

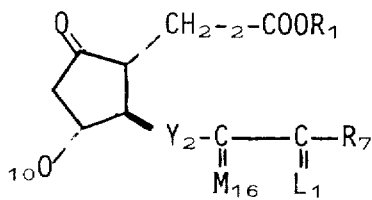  should read  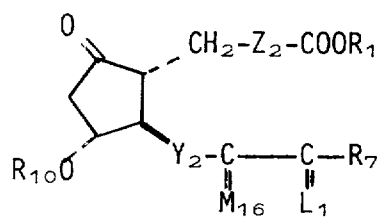

Column 19, lines 15-22, that portion of the formula reading

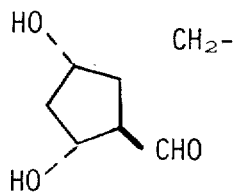  should read  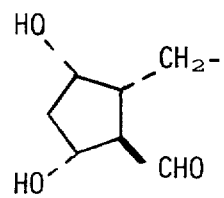

Column 25, line 35, "4 caarbon atoms" should read -- 4 carbon atoms --;

Column 35, line 2, "the various G$_1$-s of of" should read -- the various G$_1$'s of --;

Column 43, lines 14-15, "cyclopropyl cyclopentyl cyclopentylm iodide," should read -- cyclopropyl iodide, cyclopentyl iodide, --

UNITED STATES PATENT OFFICE
CERTIFICATE OF CORRECTION

Patent No. 4,028,350    Dated 7 June 1977

Inventor(s) Gordon L. Bundy

It is certified that error appears in the above-identified patent and that said Letters Patent are hereby corrected as shown below:

Column 45, line 65, "dimethyl-12-oxo-" should read -- dimethyl-2-oxo- --; line 68, "50° C." should read -- 5° C. --;
Column 46, line 19, "i cyclohexane" should read -- in cyclohexane --; line 65, "chloroide," should read -- chloride, --;
Column 48, line 19, 26, and 45, "γ-lactol" should read -- δ-lactol --; lines 41-42, "bix-tetrahydropyranyl" should read -- bis-tetrahydropyranyl --;
Column 49, line 25, "and $M_8$ is" should read -- and $M_9$ is --;
Column 54, line 1, "Following" should read -- B. Following --;
Column 55, line 54, "silic" should read -- silica --;
Column 57, line 17, "Preparation 16a" should read -- Preparation 16 --; line 28, "Formula LXXIV:" should read -- Formula LXXXIV: --; lines 39-40, "9α,11α1-epoxymethano-" should read -- 9α,11α-epoxymethano- --; line 45, "$Z_1$, $Y_1M_9$, $L_1$," should read -- $Z_1$, $Y_1$, $M_9$, $L_1$, --;
Column 58, line 59, "Preparaion 17" should read -- Preparation 17 --;
Column 66, line 17, "-Hexahydro-" should read -- Hexadehydro- --;
Column 71, line 39, "-$CH_2$-O≡C-($CH_2$)g-$CH_2$-," should read -- -$CH_2$-C≡C-($CH_2$)g-$CH_2$-, --;
Column 72, line 10, "as defeind" should read -- as defined --;
Column 73, line 1, "-O≡C-," should read -- -C≡C-, --; lines 13-15,

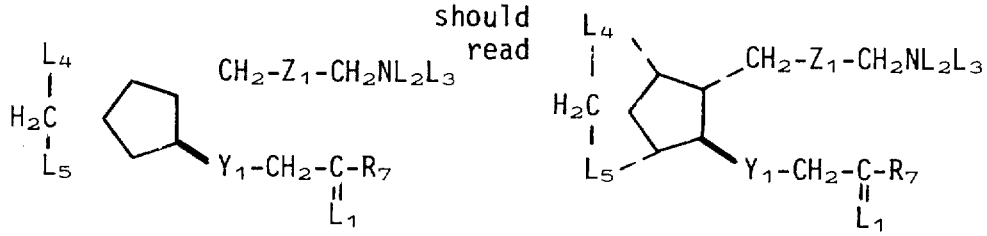

--; line 24, "cis-Ch=CH-$CH_2$-($CH_2$)g-$CF_2$-," should read -- cis-CH=CH-$CH_2$-($CH_2$)g-$CF_2$-, --; line 30, "O≡C-$CH_2$-($CH_2$)g-$CH_2$-," should read -- -C≡C-$CH_2$-($CH_2$)g-$CH_2$-, --; line 31, "-$CH_2$-O≡C-($CH_2$)g-$CH_2$-," should read -- -$CH_2$-C≡C-($CH_2$)g-$CH_2$-, --;
Column 74, lines 22-27,

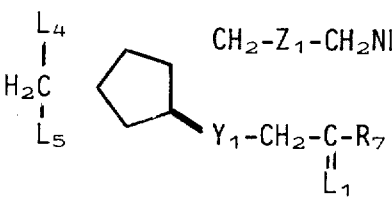

UNITED STATES PATENT OFFICE
CERTIFICATE OF CORRECTION

Patent No. 4,028,350   Dated   7 June 1977

Inventor(s)  Gordon L. Bundy

It is certified that error appears in the above-identified patent and that said Letters Patent are hereby corrected as shown below:

Column 74, line 29, "-O≡C-," should read -- -C≡C-, --; lines 42-44, 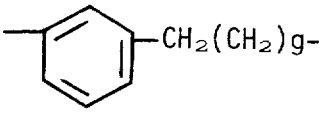 " should read -- 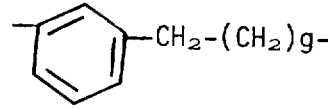 --;

Column 74, line 55, "cis-CH=Ch-Ch$_2$-(CH$_2$)g-CF$_2$-" should read -- cis-CH=CH-CH$_2$-(CH$_2$)g-CF$_2$- --; line 60, "-CH$_2$-CH-(CH$_2$-(CH$_2$)g-CH$_2$-" should read -- -CH$_2$-O-CH$_2$-(CH$_2$)g-CH$_2$- --; line 61, "-C C-CH$_2$-(CH$_2$)g-(CH$_2$-," should read -- -C≡C-CH$_2$-(CH$_2$)g-CH$_2$-, --; line 62, "(-CH$_2$-C C-(CH$_2$)g-(CH$_2$-," should read -- -CH$_2$-C≡C-(CH$_2$)g-CH$_2$-, --;

Column 75, line 43, "aminating" should read -- laminating; line 52, "L$_1$, L, L$_5$," should read -- L$_1$, L$_4$, L$_5$, --;

Column 76, line 32, "-O≡C-CH$_2$-(CH$_2$)g-CH$_2$-" should read -- -C≡C-CH$_2$-(CH$_2$)g-CH$_2$- --; line 34, "-CH$_2$-O≡C-(CH$_2$)g-CH$_2$-" should read -- -CH$_2$-C≡C-(CH$_2$)g-CH$_2$- --;

Column 77, line 37, "X$_1$ is -COOr$_1$" should read -- X$_1$ is -COOR$_1$ --;

Column 78, line 7, "-(CH$_2$)$_3$-(CH$_2$)g-(CH$_2$-" should read -- -(CH$_2$)$_3$-(CH$_2$)g-CH$_2$- --; line 11, "-(CH$_2$)$_3$-(CH$_2$)g-CD$_2$-" should read -- -(CH$_2$)$_3$-(CH$_2$)g-CF$_2$- --; line 12, "epoxymethao" should read -- epoxymethano --; line 26, "-CH$_2$-C≡C-(CH$_2$)g-(CH$_2$-" should read -- -CH$_2$-C≡C-(CH$_2$)g-CH$_2$- --; lines 33-37,

[phenyl]-CH$_2$(CH$_2$)g-    should read    [phenyl]-CH$_2$-(CH$_2$)g- line 56, "wherein R$_7$" should read -- wherein R$_7$ is --.

Signed and Sealed this

Seventeenth Day of November 1981

[SEAL]

Attest:

GERALD J. MOSSINGHOFF

Attesting Officer   Commissioner of Patents and Trademarks